(12) United States Patent
Castelhano et al.

(10) Patent No.: US 6,638,941 B1
(45) Date of Patent: Oct. 28, 2003

(54) CONFORMATIONALLLY CONSTRAINED PEPTIDOMIMETICS AS β-TURN TEMPLATES AND MODULATORS OF SH3 DOMAINS

(75) Inventors: Arlindo L. Castelhano, New City, NY (US); David J. Witter, Putnam Valley, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 09/086,168

(22) Filed: May 28, 1998

Related U.S. Application Data

(63) Continuation-in-part of application No. 08/864,241, filed on May 28, 1997, now abandoned.
(60) Provisional application No. 60/085,889, filed on May 18, 1998.

(51) Int. Cl.$^7$ .......................................... A61K 31/4427
(52) U.S. Cl. ........................... 514/278; 514/2; 514/19; 514/17; 514/18; 514/277; 514/279; 530/330; 530/331
(58) Field of Search ................ 514/2, 19, 17, 514/18, 277, 278, 279; 530/330, 331

(56) References Cited

PUBLICATIONS

Vidal M (Critical Reviews in Oncology/Hematology 40(2) 175–86, 2001).*
Mayer B J (Journal of Cell Science 114 (Pt7) 1253–63, 2001).*
Dalgarno D. C. (Biopolymers 43 (5) 383–400, 1997).*
Mayer B J (Current Topics in Microbiology and Immunology 228 1–22, 1998).*
Viallet (Lung Cancer 15 (3) 367–75, 1994).*
Kemeny (Seminars in Oncology 21 (4 Suppl 7) 67–75, 1994).*
Newton (Expert Opinion on Investigational Drugs 9 (12) 2815–29, 2000).*
Giese (Journal of Cancer Research and Clinical Oncology 127 (4) 217–25, 2001).*
Garattini (European Journal of Cancer 37 Suppl 8 S128–47, 2001).*
Ragnhammar (Acta Oncologica 40 (2□3) 282–308, 2001).*
Pilat (Oncology Reports 5(4) 889, 1998).*
Yamanashi & (Molecular and Cellular Biology 7 (1) 237–43, 1987).*
Kardinal, C. (Blood 98(6) 1773–1781, 2001).*
Lofas et al. "Spiro and Bicyclic Azalactams by Hydrolysis of α–Chlorinated Bicyclic Amidines" *J. Heterocyclic Chem* 21 p 583 (1984).

Grigg et al. "X=Y–ZY Systems as Potential 1,3–Dipoles. Part 39.1 Metallo–Azomethine Ylides from Aliphatic Aldimines. Facile Regio– and Stereo–specific Cycloaddition Reactions" *Tetrahedron* vol. 48, No. 47, p10431–10442 (1992).
Grigg et al. "X=Y–ZH Systems as Potential 1,3–Dipoles. Part 21. Activation of the ZH protn in Imines" *Tetrahedron* vol. 45 No. 6 p 1723–1746 (1989).
Grigg et al. "X=Y–ZH Systems as Potential 1,3–Dipoles. Part 21. Activation of the ZH protn in Imines" *Tetrahedron Letters* vol. 24, No. 40, p 4363–4366 (1983).
Marx et al. "Synthetic Design for Combinatorial Chemistry. Solution and Polymer–supported Synthesis of Polycyclic Lactams by Intramolecular Cyclization of Azomethine Ylides" *J. American Chemical Society* vol. 119, No. 26 p 6153–6167 (1997).
Genin et al. "Dopamine Receptor Modulation by a Highly Rigid Spiro Bicyclic Peptidomimetic of Pro–Leu–Gly–NH2" vol. 36, No. 22 p 3481–3483 (1993).
Subasinghe et al. "Stereospecific Synthesis of 2–Substituted Bicyclic Thiazolidine Lactams" *Tetrahedron Letters* vol. 38, No. 8 p 1317–1320 (1997).
Genin et al. "Design, Synthesis and X–ray Crystallographic Analysis of two Novel Spirolactam Systems as Beta–Turn Mimetics" *J. Organic Chemistry* vol. 58, No. 4 p 860–866 (1993).
Ball, J.B. and Alewood, P.F. "Conformational Constraints: Nonpeptide β–Turn Mimics" *J. Mol. Recognition* 3:55 (1990).
DeWitt et al. "'Diversomers': An Approach to Nonpeptide, Nonoligomeric Chemical Diversity" *Proc. Natl. Acad. Sci. U.S.A.* 90:6909 (1993).
Farmers, P.S. "Bridging the Gap between Bioactive Peptides and Nonpeptides: Some Perspectives in Design" *Drug Design* (E.J. Ariens, ed.) Academic Press, New York, vol. 10, chapter 3, pp. 119–143 (1980).
Feng, S. et al. "Molecular Basis for the Binding of SH3 Ligands with Non–Peptide Elements Identified by Combinatorial Synthesis" *Chemistry & Biology* 3:661–670 (1996).
Feng et al. "Two Binding Orientations for Peptides to the Src SH3 Domain: Development of a General Model for SH3–Ligand Interactions" *Science* 266:1214–1247 (1994).
Giannis, A. and Kolter, T. "Peptidomimetics for Receptor Ligands—Discovery, Development, and Medical Perspectives" *Angew. Chem. Int. Ed. Engl.* 32:1244–1267 (1993).

(List continued on next page.)

*Primary Examiner*—Christopher S. F. Low
*Assistant Examiner*—David Lukton
(74) *Attorney, Agent, or Firm*—John P. White; Cooper & Dunham LLP

(57) ABSTRACT

Spirolactam compounds useful as inhibitors of protein-protein interactions modulated by SH3 domains are disclosed. Compounds of the invention are also useful as β-turn mimetics. Also disclosed are libraries of compounds of the invention, pharmaceutical compositions of the compounds of the invention, and methods for using the compounds of the invention to inhibit growth of a cell or to inhibit protein-protein interactions modulated by SH3 domains.

24 Claims, No Drawings

OTHER PUBLICATIONS

Goodman, M. and Chorez, M. "The Synthesis and Conformational Analysis of Retro–Inverso Analogues of Biologically Active Molecules" *Perspectives in Peptide Chemistry*, pp. 283–294 (1981).

Gordon, E.M. et al. "Applications of Combinatorial Technologies to Drug Discovery. 2. Combinatorial Organic Synthesis, Library Screening Strategies, and Future Directions" *Journal of Medicinal Chemistry* 37(10):1385–1401 (1994).

Gorina, S. et al. "Structure of the p53 Tumor Suppressor Bound to the Ankyrin and SH3 Domains of 53BP2" *Science* 274:1001–1005 (1996).

Goudreau et al. "NMR Structure of the N–terminal SH3 Domain of GRB2 and Its Complex with a Proline–rich Peptide from Sos" *Structural Biology* 1(12) 898–907 (1994).

Grzesiek, S. et al. "The Solution Structure of HIV–1 Nef Reveals an Unexpected Fold and Permits Delineation of the Binding Surface for the SH3 Domain of Hck Tyrosine Protein Kinase" *Nature Structural Biology* 3(4):340–345 (1996).

James, G.L. et al. "Benzodiazepine Peptidomimetics: Potent Inhibitors of Ras Farnesylation in Animal Cells" *Science* 260:1937–1942 (1993).

Khalil, E. et al. "Design, Synthesis and Conformational Analysis of Spiro–Bicyclic Lactams as Type II β–Turn Mimetics" *Diss. Abstr. Int.* 58(7):3638–3640 (1998).

Lee, C.–H. et al. "Crystal Structure of the Conserved Core of HIV–1 Nef Complexed with a Arc Family SH3 Domain" *Cell* 85:931–942 (1996).

Ramakrishnan, C. et al. "Motifs and Conformational Analysis of Amino Acid Residues Adjoining β–Turns in Proteins" *International Journal of Peptide & Protein Research* 48:420–428 (1996).

Reich, V. et al. "The Basolateral Sorting Signal of the Polymeric Immunoglobulin Receptor Contains Two Funtional Domains" *Journal of Cell Science* 109:2133–2139 (1996).

Renzoni, D.A. et al. "Structural and Thermodynamic Characterization of the Interaction of the SH3 Domain from Fyn with the Proline–Rich Binding Site on the p85 Subunit of PI3–Kinase" *Biochemistry* 35:15646–15653 (1996).

Seebach, D. et al. "Alkylation of Amino Acids without Loss of the Optical Activity: Preparation of α–Substituted Proline Derivatives. A Case of Self–Reproduction of Chirality" *J. Am. Chem. Soc.* 105:5390–5398 (1983).

Smithgall, T.E. "SH2 and SH3 Domains: Potential Targets for Anti–Cancer Drug Design" *Journal of Pharmacological and Toxicological Methods* 34:125–132 (1995).

Viguera, A.R. et al. "Conformational Analysis of Peptides Corresponding to β–Sheet that Prepresent the Entire Sequence of the α–Spectrin SH3 Domain" *Journal of Molecular Biology* 255:507–521 (1996).

Wu et al. "Strucural Basis for the Specific Interaction of Lysine–containing Proline–rich Peptides with the N–Terminal SH3 Domain of c–Crk" *Structure* 3:215–226 (1995).

* cited by examiner ated "Conformationally Constrained Peptidomimetics as β-Turn Templates and Modulators of SH3 Domains", and is a continuation-in-part of U.S. Ser. No. 08/864,241, entitled "Conformationally Constrained Peptidomimetics as β-Turn Templates and Modulators of SH3 Domains", filed on May 28, 1997, now abandoned the contents of which are hereby expressly incorporated by reference.

CONFORMATIONALLLY CONSTRAINED PEPTIDOMIMETICS AS β-TURN TEMPLATES AND MODULATORS OF SH3 DOMAINS

RELATED APPLICATIONS

This application claims the benefit of U.S. Provisional Application Serial No. 60/085,889, filled May 18, 1998, entitled "Conformationally Constrained Peptidomimetics as β-Turn Templates and/Modulators of SH3 Domains", and is a continuation-in-part of U.S. Ser. No. 08/864,241, entitled "Conformationally Constrained Peptidomimetics as β-Turn Templates and Modulators of SH3 Domains", filed on May 28, 1997, now abandoned the contents of which are hereby expressly incorporated by reference.

BACKGROUND OF THE INVENTION

Over the years, peptidomimetics have become immensely important for both organic and medicinal chemists, as well as the pharmaceutical industry due to the multitude of biological active peptides discovered and characterized. Peptidomimetics are currently exploited to overcome problems associated with their parent peptides (for review, see, e.g. reference 28). These improvements include increased selectivity, oral bioavailability and prolonging the activity by hindering enzymatic degradation within the organism. Among the class of peptidomimetics are the mimetics of protein secondary structure.

Retention of peptide secondary structure is an important tool in drug research when applied to fixing the active conformation of a protein. Constraining the structure of a peptide in its biologically active conformation increases its activity or binding. Within the realm of secondary structures are protein β-turns, which have attracted the attention of medicinal chemists due its importance in such events as hormone-receptor and peptide-enzyme recognition. The β-turn is a segment composed of four amino acids (i to i+1) that occurs when a peptide strand changes its direction. In areas, such as cellular signal transduction, protein-protein interactions are known to be crucial for proper signaling, and may find application for protein β-turn mimetics.

Cellular signal-transduction pathways that are initiated by transmembrane receptors associating with cytoplasmic protein kinases rely on two small protein domains containing sequences of 50–100 amino acids each. These sequences, referred to as Src homology 2 (SH2) and Src homology 3 (SH3) domains, can fold into modules which interact independently of their surrounding sequences. Because SH2 and SH3 domains are involved in protein-protein interactions in the signal transduction pathway, they represent potential targets for therapeutic drugs.

The nature of the interaction between SH3 domains and proteins has been the subject of recent study. The three-dimensional structure of SH3/peptide complexes have been extensively investigated (5–16). These reports revealed that SH3 domains interact with protein ligands via hydrophobic contacts on the surface of the domain and protein. These domains have preferences for certain sequences of amino acids, as determined by screening against peptide combinatorial libraries. The protein ligands form a polyproline type II (PPII) left-handed α-helix containing a consensus sequence that can be generalized as XPpXP, where X is an aliphatic amino acid and p is preferably proline to maintain the helix.

All reported naturally-occurring SH3 ligands are peptides, although certain non-natural SH3 ligands have been described. A variety of peptidomimetics have been described, some of which mimic the β-turn motif (for a review, see, e.g., reference 28). However, no peptidomimetic has been reported to modulate activity of SH3 domains. In a study by Feng et al., a biased combinatorial library was constructed by functionalizing the N-terminus of a pentapeptide with various non-peptide elements, and the constructs were assayed for binding with Src SH3 domain (17). The nonpeptidic moieties appeared to interact with the specificity pocket of Src SH3 domain, lowering the $k_d$ almost 1000-fold from the parent pentapeptide (>1000 mM to 3.4 mM). However, to date, few if any non-peptidic ligands binding in the hydrophobic pockets of SH3 domains have been discovered.

The β-turn has attracted the attention of medicinal chemists due to its importance in such events as hormone-receptor and peptide-enzyme recognition. Rapid degradation of natural peptide substrate or ligands containing the β-turn have lead to the design of compounds mimicking this secondary structure (19, 24–28, 29). A tricyclic compound which includes a 5,6-spirolactam moiety has been described as a Type II β-turn mimetic (A. M. Khalil et al., 25th National Medicinal Chemistry Symposium, University of Michigan, 1996). The configuration of the compound so prepared is reported to provide a β-turn-type structure, rather than an extended conformation.

SUMMARY OF THE INVENTION

This invention pertains to peptide mimetics including peptide β-turn mimetics, to compositions which include the peptide β-turn mimetics of the invention, and to methods for inhibiting protein-protein interactions with SH3 domains.

In one aspect, the invention provides a compound represented by the formula (Formula I):

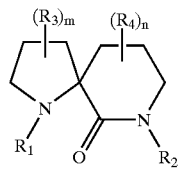

in which

R$_1$ is hydrogen, alkyl, aryl, alkylcarbonyl, arylcarbonyl, aminocarbonyl, alkoxycarbonyl, aryloxycarbonyl, alkylsulfonyl, arylsulfonyl, or an amino acyl group (e.g., an amino acid residue or a peptide segment);

R$_2$ is hydrogen, alkyl, aryl, or —C(R$_{2a}$)(R$_{2b}$)C(O)R$_5$;

R$_{2a}$ and R$_{2b}$ are each independently hydrogen, alkyl, or aryl; or, R$_{2a}$ and R$_{2b}$, taken together with the carbon atom to which they are attached, form a 3 to 8 membered carbocyclic or heterocyclic ring;

R$_3$ and R$_4$ are each, independently for each occurrence, hydrogen, halogen, alkyl, amino, hydroxy, alkoxy, cyano, or trifluoromethyl; or R$_{2a}$ and R$_4$, together with the atoms to which they are attached, form a 5 or 6-membered heterocyclic ring;

R$_5$ is hydroxy, alkyl, aryl, amino, alkoxy, aryloxy, —SH, alkylthio, arylthio or an amino acyl group (e.g., an amino acid residue or a peptide segment);

m and n are each independently 1 or 2; or a salt thereof.

In a preferred embodiment, R$_1$ is a tetrapeptide, more preferably Ac-Pro-Arg-Pro-Leu or Ac-Ala-Pro-Ala-Leu. In another embodiment, R$_1$ is an amino acyl residue selected from the group consisting of Boc-Leu and Boc-Val. In still other embodiments, $R_1$ is an aminocarboxy moiety represented by the formula —C(O)NHR$_7$, in which $R_7$ is an aryl moiety or a bulky alkyl group. In preferred embodiments, $R_2$ is a moiety represented by the formula —C(R$_{2a}$)(R$_{2b}$)C(O)R$_5$. In preferred embodiments, $R_{2b}$ is hydrogen and $R_{2a}$ is a side-chain moiety of a naturally occurring amino acid. In preferred embodiments, $R_5$ is a tripeptide moiety selected from the group consisting of Lys-Pro-Pro-OH and Ala-Pro-Gly-OH. In preferred embodiments, $R_3$ is hydroxy.

In another embodiment, the invention provides a compound represented by the formula (Formula Ia):

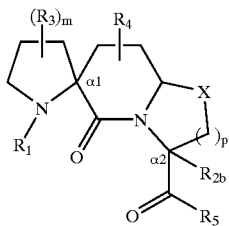

in which
X is —CH$_2$—, S or O;
$R_1$ is hydrogen, alkyl, aryl, alkylcarbonyl, arylcarbonyl, aminocarbonyl, alkoxycarbonyl, aryloxycarbonyl, alkylsulfonyl, arylsulfonyl, or an amino acyl group;
$R_{2b}$ is hydrogen, alkyl, or aryl;
$R_3$ and $R_4$ are each, independently for each occurrence, hydrogen, halogen, alkyl, amino, hydroxy, alkoxy, cyano, or trifluoromethyl;
$R_5$ is hydroxy, alkyl, aryl, amino, alkoxy, aryloxy, —SH, alkylthio, arylthio or an amino acyl group;
m and p are each, independently, 1 or 2; or a salt thereof; with the proviso that if X is S, p is 1, and R$_{2b}$ is hydrogen, then the configuration at the carbon atom to which R$_{2b}$ is attached is not the R configuration.

In preferred embodiments, $R_{2b}$ is hydrogen.

In another aspect, the invention provides a method for inhibiting a protein-protein interaction mediated by an SH3 domain. The method includes the step of contacting the SH3 domain with a compound of Formula I, such that a protein-protein interaction mediated by an SH3 domain is inhibited. In preferred embodiments, $R_1$ is a tetrapeptide, more preferably Ac-Pro-Arg-Pro-Leu or Ac-Ala-Pro-Ala-Leu. In preferred embodiments, $R_1$ is an amino acyl residue selected from the group consisting of Boc-Leu and Boc-Val. In other embodiments, $R_1$ is an aminocarboxy moiety represented by the formula —C(O)NHR$_7$, in which $R_7$ is an aryl moiety or a bulky alkyl group. In preferred embodiments, $R_2$ is a moiety represented by the formula —C(R$_{2a}$)(R$_{2b}$)C(O)R$_5$. In preferred embodiments, $R_{2b}$ is hydrogen and $R_{2a}$ is a side-chain moiety of a naturally occurring amino acid. In preferred embodiments, $R_5$ is a tripeptide moiety selected from the group consisting of Lys-Pro-Pro-OH and Ala-Pro-Gly-OH.

In another aspect, the invention provides a method for inhibiting growth of a cell. The method includes the step of contacting the cell with an effective amount of a compound of Formula I such that growth of the cell is inhibited. In a preferred embodiment, the compound is a compound of Formula Ia.

In another aspect, the invention provides a method for inhibiting a protein-protein interaction mediated by an SH3 domain. The method includes the step of contacting an SH3 domain with an effective amount of a compound of Formula I, such that a protein-protein interaction mediated by an SH3 domain is inhibited. In a preferred embodiment, the SH3 domain is an SH3 domain of Lyn.

In another aspect, the invention provides a library of compounds of Formula I, more preferably a library of compounds of Formula Ia.

In another aspect, the invention provides a pharmaceutical composition. The pharmaceutical composition includes a compound of Formula I (more preferably a compound of Formula Ia), or a pharmaceutically acceptable salt thereof, in a pharmaceutically acceptable vehicle.

DETAILED DESCRIPTION OF THE INVENTION

The present inventors have now investigated various known SH3/peptide complexes to design a template that could be exploited for drug discovery. Surveying the conformations of the protein ligands, it was determined (e.g., by molecular modeling) that bound conformations of the ligands differed from minimized unbound peptides (Table 1).(9, 10, 12). Generally, small peptides exhibit little or no conformational preference. However, the inventors have now recognized that bound ligands often appear to exhibit an extended conformation.

TABLE 1

Reported SH3 Domain Structures.

| Protein | Technique | Reference | Reference |
|---|---|---|---|
| Src | NMR | (9) | Feng et al. Science 1994, 1241–1247. |
| HIV-1 Nef with Src | X-ray | (16) | Lee et al. Cell 1996, 931–942. |
| α-Spectrin | NMR | (5) | Viguera et al J.Mol.Biol 1996, 507–521. |
| PI3K | NMR | (8) | Yuetal et al. Cell 1994, 933–945. |
| 53BP2 | X-ray | (7) | Gorina et al. Science 1996, 1001–1005 |
| Hck/HIV-1 Nef | NMR | (6) | Grzesiek et al Nature Struct. Biol. 1996, 340–345 |
| Grb2 | NMR | (10) | Goudreau et al Nature Struct. Biol. 1994, 898–907 |
| Fyn | X-ray | (15) | Musacchio et al. Nature Struct. Biol. 1994, 546–551. |
| Ab1 | X-ray | (15) | Musacchio et al. Nature Struct. Biol. 1994, 546–551. |
| Grb-2 N-terminal SH3 domain | X-ray | (13, 14) | Terasawa et al. Nature Struct. Biol. 1994, 891–897. Wittekind et al. Biochemistry 1994, 13531–13539. |
| Sem-5 C-terminal SH3 domain | X-ray | (11) | Lim et al. Nature 1994, 375–379. |
| Crk | X-ray | (12) | Wu et al. Structure 1995, 215–226. |

It is believed that the unbound peptide ligand relieves A(1–3) strain from the αC—H and the N-δCH$_2$ bonds in prolines 1 and 2, respectively, in the XPpXP motif, by rotating about the αC—C(O) bond. Preferably, a synthetic ligand can incorporate this conformational bias. Free rotation around the αC—C(O) bond can be locked by inserting a methylene bridge between the Pro-1 α—C and the Pro-2 N, (See diagram below) resulting in a spirolactam structure, e.g., the 5,6-spirolactam structure of the compounds of the invention. The invention is based, at least in part, on the understanding that by exploiting the conformational difference between bound and unbound ligand, compounds containing the inventive spirolactam moiety instead of the Pro-Pro dipeptide of natural SH3 domain ligands (i.e., the Pp portion of the XPpXP sequence) can gain binding affinity from the subsequent loss of flexibility.(18) The spirolactam template of the invention is believed both to mimic the Pp portion of the consensus sequence, and also to resemble a protein β-turn structure, a common motif of biologically active peptides. (19–23).

the N- or the C-terminus (or both) to construct a library of compounds containing the β-turn element. The resultant libraries are also valuable for the generation of lead compounds targeted at specific SH3 domains and other protein-protein interactions, e.g., as described herein.

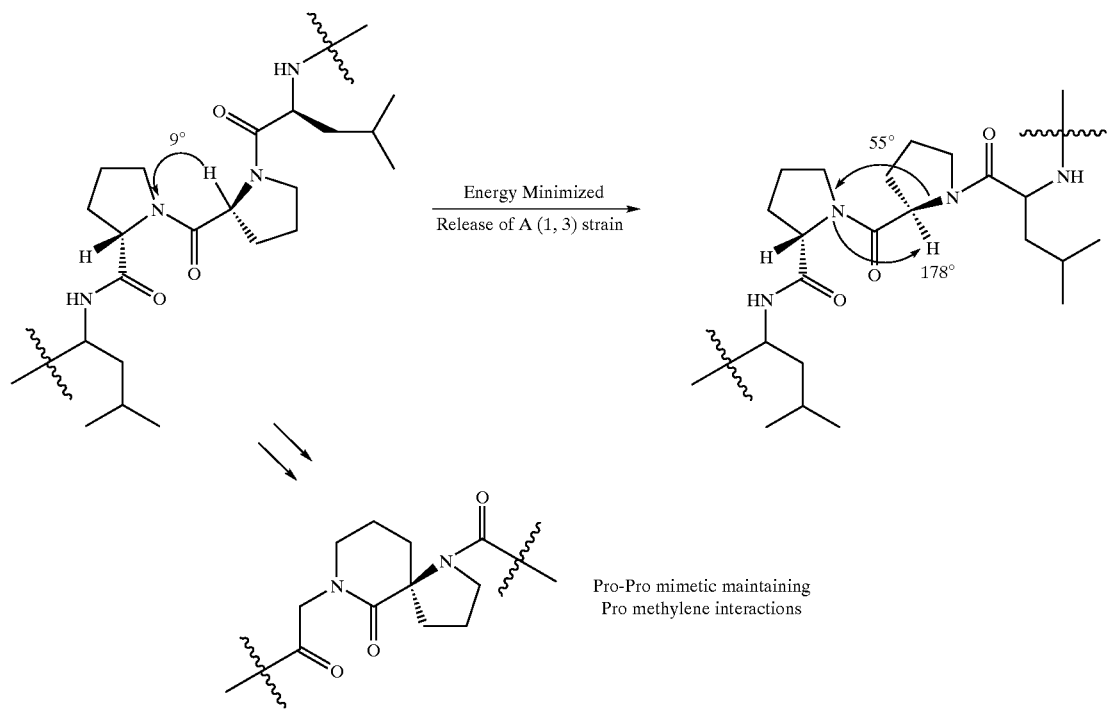

Pro-Pro mimetic maintaining
Pro methylene interactions

The novel 5,6 spirolactams of the invention incorporate a rigid structure around which the N- and C-terminal ends allow for functionalization, and change "direction" of the ligand, as seen in the β-turn motif.

A 5,6 spirolactam of Formula I incorporates a rigid structure around which positions $R_1$, $R_2$, $R_3$ and $R_4$ can be modified to construct a library of compounds diverse in functionality. As shown in Table 2, the various functionalities at the $R_1$ position can be selected to provide ureas, amides (including, e.g., amino acids and small peptide segments), and sulfonamides at the "N-terminal" portion of the spirolactam moiety. The $R_2$ position can be modified during the synthesis of the spirolactam using different amino acids. The $R_5$ substituent can be selected to provide a "C-terminal" free acid, esters, or amides. The amides can be prepared, e.g., from coupling with 1°, 2° amines, amino acids, or peptides. Exemplary modifications are shown in Table 2. The N-terminal amine can be unsubstituted ($R_1$=H), or, as shown in Table 2, substituted with a variety of functionalities ($R_1$), including peptides, amino acids (which can be protected amino acids), aminocarbonyl groups (providing a compound with an N-terminal urea functionality), and sulfonyl groups. The $R_{2a}$ functionality can be, e.g., hydrogen or an amino acid side chain (e.g., of alanine, isoleucine, lysine, glutamic acid, phenylalanine or tyrosine). The $R_5$ moiety can be, e.g., a peptide, an amino acid, a hydroxy, alkoxy, or aryl group (providing a C-terminal acid or ester functionality), or a primary or secondary amino group (providing a C-terminal amide functionality).

Thus, as discussed in more detail infra, the novel 5,6-spirolactams of the invention can be functionalized at either

TABLE 2

Examples of Various Functionalities at Positions $R_1$, $R_{2a}$ and $R_5$ $R_1$ Peptides eg.

Ac-Pro-Arg-Pro-Leu
Ac-Ala-Pro-Ala-Leu
Amino Acids eg.

Boc-Leu
Boc-Val
Ureas eg.

TABLE 2-continued

Examples of Various Functionalities at Positions $R_1$, $R_{2a}$ and $R_5$

[Structures shown: N-formyl-2-phenylcyclopropylamine; N-formyl-2,5-dichloroaniline; N-formyl-4-bromoaniline; N-formyl-4-methoxy-2-methoxyaniline (H₃CO- and -OCH₃); N-formyl-2,4-dimethylaniline; 4-chlorobenzenesulfonyl formamide; N-formyl-4-acetylaniline; 2-methylbenzenesulfonyl formamide; N-formyl-tert-butylamine; N-formyl-n-butylamine; N-formyl-2,4,4-trimethylpentan-2-amine]

N-formyl-cyclohexylamine

Sulfonamides eg.

[benzyl sulfone structure]

---

$R_{2a}$

Alkyl eg.

H
CH₃

[isobutyl structure]

[sec-butyl structure]

Substituted eg.

[H₂N-butyl structure]

[propyl guanidine structure]

[propanoic acid]

[acetic acid]

[propanamide]

[acetamide]

Aromatic eg

[phenyl]

[4-hydroxyphenyl]

TABLE 2-continued

Examples of Various Functionalities at Positions $R_1$, $R_{2a}$ and $R_5$ $R_5$ Peptides eg.

Lys-Pro-Pro-OH
Ala-Pro-Gly-OH
Amino Acids eg.

Leu-OH
Val-OH
Esters eg.

OH
$OCH_3$
O-Alkyl
O-Aromatic
1° and 2° Amides eg.

DEFINITIONS

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term "alkyl" as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "aryl" as used herein includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The terms "heterocyclyl" or "heterocyclic group" refer to 3- to 10-membered ring structures, more preferably 4- to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, cyclic anhydrides, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, aralkyl, or an aromatic or heteroaromatic moiety.

The terms "polycyclyl" or "polycyclic group" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, aralkyl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "amino" as used herein, refers to a moiety represented by the formula —$NR_aR_b$, in which $R_a$ and $R_b$ are each independently hydrogen, alkyl, aryl, or heterocyclyl, or $R_a$ and $R_b$ together with the nitrogen atom to which they are attached, form a 3- to 8-membered heterocyclic ring.

The term "linker group," as used herein, refers to a linking or spacing moiety which can be used to covalently or non-covalently link a compound to a solid support. Linker groups suitable for use in the invention are known in the art for use in solid-phase synthesis. It will be appreciated by the skilled artisan that a linker group can be a direct bond to a solid support, such a resin bead.

The term "amino acid," as used herein, refers to naturally-occurring amino acids, as well as to analogs, derivatives, and mimetics thereof. The SH3 domain inhibitor compounds of the present invention can also comprise peptide analogs, peptide derivatives (e.g.,), and peptidomimetics. As used herein, a "derivative" of a compound X (e.g., a peptide) refers to a form of X in which one or more reaction groups on the compound have been derivatized with a substituent group (e.g., alkylated or acylated peptides). As used herein an "analog" of a compound X refers to a compound which retains chemical structures of X necessary for functional activity of X yet which also contains certain chemical structures which differ from X. An examples of an analog of a naturally-occurring peptide is a peptide which includes one or more non-naturally-occurring amino acids. As used herein, a "mimetic" of a compound X refers to a compound in which chemical structures of X necessary for functional activity of X have been replaced with other chemical structures which mimic the conformation and function of X. Examples of peptidomimetics include peptidic compounds in which the peptide backbone is substituted with one or more benzodiazepine molecules (see e.g., James, G. L. et al. (1993) *Science* 260:1937–1942) and "retro-inverso" peptides (see U.S. Pat. No. 4,522,752 by Sisto), described further below. A "residue" refers to an amino acid or amino acid mimetic incorporated in the peptide compound by an amide bond or amide bond mimetic. Approaches to designing peptide derivatives, analogs and mimetics are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270.

An "amino acid mimetic" refers to a moiety, other than a naturally occurring amino acid, that conformationally and functionally serves as a substitute for a particular amino acid in a peptide-containing compound without adversely interfering to a significant extent with the function of the compound (e.g., binding to an SH3 domain). In some circumstances, substitution with an amino acid mimetic may actually enhance properties of the compound (e.g., interaction of the compound with the SH3 domain). Examples of amino acid mimetics include D-amino acids. Peptides substituted with one or more D-amino acids may be made using well known peptide synthesis procedures. The effect of amino acid substitutions with D-amino acids and other peptidomimetics can be tested using assays as described infra.

The peptide analogs or mimetics of the invention include isosteres. The term "isostere" as used herein refers to a sequence of two or more residues that can be substituted for a second sequence because the steric conformation of the first sequence fits a binding site specific for the second sequence. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[C(S)NH$_2$], ψ[NHCO], ψ[C(O)CH$_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al. (1993) *Science* 260:1937–1942).

Other possible modifications include an N-alkyl (or aryl) substitution (ψ[CONR]), backbone crosslinking to construct lactams and other cyclic structures, or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide and is able to bind the selected SH3 domain. See Goodman et al. *"Perspectives in Peptide Chemistry"* pp. 283–294 (1981). See also U.S. Pat. No. 4,522,752 by Sisto for further description of "retro-inverso" peptides.

In addition to amino acid-substituted inhibitor compounds, the invention also encompasses SH3 domain inhibitor compounds having other modifications. For example, the amino-terminus of an amino acid or peptide substituent can be modified. The term "amino-derivative group" is intended to include amino-terminal modifications of the peptide-containing compounds of the invention. Examples of N-terminal modifications include alkyl, cycloalkyl, aryl, araalkyl, and acyl groups. A preferred N-terminal modification is acylation. Preferred N-terminal acyl or acyloxy groups include acetyl (denoted Ac), and benzoyl, as well as acyloxy groups such as methoxycarbonyl, t-butoxycarbonyl and benzyloxycarbonyl (also denoted "Cbz"). The N-terminal residue may be linked to a variety of moieties other than amino acids such as polyethylene glycols (such as tetraethylene glycol carboxylic acid monomethyl ether), pyroglutamic acid, succinoyl, methoxy succinoyl, benzoyl, phenylacetyl, 2-, 3-, or 4-pyridylalkanoyl, aroyl, alkanoyl (including acetyl and cycloalkanoyl e.g., cyclohexylpropanoyl), arylalkanoyl, arylaminocarbonyl, alkylaminocarbonyl, cycloalkylaminocarbonyl, alkyloxycarbonyl (carbamate caps), and cycloalkoxycarbonyl, among others.

Except as otherwise noted, standard abbreviations are used throughout this disclosure when describing peptide substituents of the compounds of the invention.

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

The term "solid support," as used herein, refers to a solid or insoluble phase which can serve as a support or "scaffold" for the preparation of functionalized compounds by solid-phase chemistry. Many solid supports are known in the art and some are commercially available. Exemplary solid supports include cross-linked divinylbenzene-styrene (polystyrene), controlled pore glass (CPG), polyacrylamides, poly(ethyleneglycol)monomethyl ether and poly(ethylene glycol) (PEG), silica gel, cellulose, acrylic acid grafted polypropylene, and the like. Commercially-available solid supports include Wang resin, Merrifield resin, Tentagel, Rapp resin, and the like.

The term "subject", as used herein, refers to an animal, more preferably a warm-blooded animal, most preferably a mammal, including cattle, sheep, pigs, horses, dogs, cats, rats, mice, and humans.

The term "SH3 domain" is art-recognized, and, as used herein, refers to a protein domain involved in protein-protein interactions, such as a domain of a Src tyrosine kinase that negatively regulates kinase activity. Several SH3 domains have been reported and are typically associated with a regulatory function. The invention contemplates modulation of activity, such as activity dependent upon protein-protein interactions, mediated by SH3 domains of proteins (e.g., tyrosine kinases such as src, or proteins involved with transmission of a tyrosine kinase signal, such as Grb2) from organisms including mammals, including humans. For examples of SH3 domains, see the discussion and references cited supra and, e.g., Smithgall, T. E. *J. Pharmacol. Toxicol. Methods* 1995 34:125–132).

The language "modulating an activity mediated by an SH3 domain" as used herein, refers to inhibiting, abolishing or increasing the activity of a cell-signalling pathway mediated by a protein including an SH3 domain, e.g., by disrupting protein-protein interactions mediated by SH3 domains. In a preferred embodiment, an activity mediated by an SH3 domain is inhibited, for example, an interaction of GRB2 and SOS is inhibited.

It will be noted that the structure of some of the compounds of this invention include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, alkenes can include either the E- or Z-geometry, where appropriate.

I. Compounds

In one aspect, the invention provides spirocyclic compounds useful as ligands for, and modulators of interactions mediated by, SH3 domains.

In one embodiment, the invention provides a compound represented by the formula (Formula I):

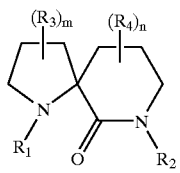

in which
- $R_1$ is hydrogen, alkyl, aryl, alkylcarbonyl, arylcarbonyl, aminocarbonyl, alkoxycarbonyl, aryloxycarbonyl, alkylsulfonyl, arylsulfonyl, or an amino acyl group (including, e.g., an amino acid residue or a peptide segment);
- $R_2$ is hydrogen, alkyl, aryl, or —$C(R_{2a})(R_{2b})C(O)R_5$;
- $R_{2a}$ and $R_{2b}$ are each independently hydrogen, alkyl, or aryl; or, $R_{2a}$ and $R_{2b}$, taken together with the carbon atom to which they are attached, form a 3 to 8 membered carbocyclic or heterocyclic ring;
- $R_3$ and $R_4$ are each, independently for each occurrence, hydrogen, halogen, alkyl, amino, hydroxy, alkoxy, cyano, or trifluoromethyl; or $R_{2a}$ and $R_4$, together with the atoms to which they are attached, form a 5 or 6-membered heterocyclic ring;
- $R_5$ is hydroxy, alkyl, aryl, amino, alkoxy, aryloxy, —SH, alkylthio, arylthio or an amino acyl group (e.g., an amino acid residue or a peptide segment);
- m and n are each independently 1 or 2; or a salt thereof.

In a preferred embodiment, $R_1$ is an amino acyl residue. Thus, for example, $R_1$ can be an amino acid residue, or a polypeptide. In a preferred embodiment, $R_1$ is a peptide, preferably a tetrapeptide. In a particularly preferred embodiment, the tetrapeptide has the formula Ac-Pro-Arg-Pro-Leu or Ac-Ala-Pro-Ala-Leu. In other embodiments, $R_1$ is an amino acyl residue such as Boc-Leu or Boc-Val. In still other embodiments, $R_1$ is an aminocarboxy moiety represented by the formula —$C(O)NHR_7$, in which $R_7$ is preferably an aryl moiety or a bulky alkyl group, e.g., a branched alkyl group. In still another embodiment, $R_1$ is an alkylsulfonyl or arylsulfonyl moiety.

In a preferred embodiment, $R_2$ is a moiety represented by the formula —$C(R_{2a})(R_{2b})C(O)R_5$. In a preferred embodiment, $R_{2b}$ is hydrogen and $R_{2a}$ is a side-chain moiety of a naturally occurring amino acid., e.g., a methyl group, an isobutyl group, a phenylmethyl group, and the like. In preferred embodiments, $R_5$ is an amino acyl moiety, more preferably a peptide or polypeptide moiety. In a preferred embodiment, $R_5$ is a tetrapeptide moiety, most preferably Lys-Pro-Pro-OH or Ala-Pro-Gly-OH. In certain embodiments, $R_5$ is hydroxy, alkoxy, or aryloxy. In another embodiment, $R_5$ is an amino group, preferably a monoalkylamino group in which the alkyl group is branched or substituted with one or more aryl moieties. In a preferred embodiment, both $R_3$ and $R_4$ are hydrogen for all occurrences. However, in certain embodiments, $R_3$ is hydroxyl.

In a preferred embodiment, the compound of Formula I has the S configuration at the spirocyclic carbon atom. In other embodiments, the compound of Formula I has the R configuration at the spirocyclic carbon atom. In a preferred embodiment, neither $R_{2a}$ nor $R_{2b}$ is joined with $R_4$ to form a ring structure.

In a preferred embodiment, $R_2$ is a moiety represented by the formula —$C(R_{2a})(R_{2b})C(O)R_5$, and $R_{2a}$ and an $R_4$ moiety, together with the atoms to which they are attached, form a 5 or 6-membered heterocyclic ring, with the proviso that if X is S, p is 1, and $R_{2b}$ is hydrogen, then the configuration at the carbon atom to which $R_{2b}$ is attached (the carbon labeled α2), is not the R configuration (i.e., the configuration of D-cysteine). In one particularly preferred embodiment, a compound of the invention can be represented by the formula (Formula Ia):

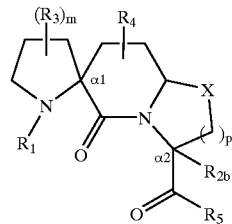

in which m, $R_1$, $R_{2b}$, $R_3$, $R_4$ and $R_5$ are as described above, X is —$CH_2$—, S, or O, and p is 1 or 2.

In a preferred embodiment, $R_1$ is an amino acyl residue. Thus, for example, $R_1$ can be an amino acid residue, or a polypeptide. In a preferred embodiment, $R_1$ is a peptide, preferably a tetrapeptide. In a particularly preferred embodiment, the tetrapeptide has the formula Ac-Pro-Arg-Pro-Leu or Ac-Ala-Pro-Ala-Leu. In other embodiments, $R_1$ is an amino acyl residue such as Boc-Leu or Boc-Val. In still other embodiments, $R_1$ is an aminocarboxy moiety represented by the formula —$C(O)NHR_7$, in which $R_7$ is preferably an aryl moiety or a bulky alkyl group, e.g., a branched alkyl group. In still another embodiment, $R_1$ is an alkylsulfonyl or arylsulfonyl moiety.

In a preferred embodiment, of the compound of Formula Ia, the configuration at the two ring junction chiral carbons (labeled as α1 and α2) is the same, i.e., α1 and α2 are both R or both S in configuration, more preferably both S. In a preferred embodiment, $R_{2b}$ is hydrogen. In preferred embodiments, $R_5$ is an amino acyl moiety, more preferably a peptide or polypeptide moiety. In a preferred embodiment, $R_5$ is a tripeptide moiety, most preferably Lys-Pro-Pro-OH or Ala-Pro-Gly-OH. In certain embodiments, $R_5$ is hydroxy, alkoxy, or aryloxy. In another embodiment, $R_5$ is an amino group, preferably a monoalkylamino group in which the alkyl group is branched or substituted with one or more aryl moieties.

In some cases, compounds having fewer amino acid residues are more easily and economically prepared, and are more stable, than compounds which include more amino acid residues. Thus, in preferred embodiments, a compound of Formula I comprises no more than about 7 amino acid residues (e.g., $R_1$ and $R_2$, or $R_1$ and $R_5$, together do not include more than about 7 amino acid residues), more preferably not more than about 5 amino acid residues, and still more preferably not more than about 3 amino acid residues.

The compounds of the invention can be prepared by the methods described herein, or by other methods which will be routine for the ordinarily skilled artisan in light of the teachings herein. For example, the spirocyclic compounds of the invention can be prepared from chiral or non-chiral starting materials, and can be enantiomerically pure or a racemic mixture of compounds. Although the synthesis described in Example 1 produces a racemic modification (e.g., racemization occurs at the alkylation step), enantiomeric purity can be retained through the alkylation step by means of "self-reproduction" of chirality (see, e.g., Seebach, D. et al. *J. Am. Chem. Soc.* (1983) 105:5390–5398). Alternatively, chiral auxiliaries or catalysts can be employed to obtain enantiomerically enriched products. Enantiomers can also be separated by resolution techniques, such as chiral chromatography or the use of chiral acids or bases, as are conventional in the art.

Furthermore, analogs and derivatives of the compounds of the invention can be prepared by standard synthetic methodologies in light of the teachings herein. Thus, for example, substitution of an appropriately-protected 3- or 4-hydroxyproline (3- and 4-hydroxyproline are available, e.g., from Sigma Chemical Co., St. Louis, Mo.) in place of proline in the synthesis described in Example 1, provides compounds of the invention, e.g., in which $R_3$ is a hydroxy group (or a derivative thereof) and m is one.

It will be appreciated by the skilled artisan that the conformation of the spirolactam peptidomimetics of the invention can be altered by appropriate selection of substituents and configuration (e.g., chiral configuration) of the substituents selected. The configuration of the ring junction carbons can also affect the conformation of the peptidomimetics of the invention. Thus, for example, in compounds of Formula Ia, the configuration of the carbon atom to which the —$C(O)R_5$ moiety is attached (the carbon atom labeled as α2 in Formula Ia), can affect the conformation of the peptidomimetic; one epimer at the α2 carbon can assume the β-turn structure, while the other epimer at the α2 carbon can assume an extended conformation, i.e., a conformation which may be useful as an SH3 domain modulator. In a preferred embodiment, a compound of the invention has an extended conformation and/or is capable of modulating protein-protein interactions mediated by an SH3 domain.

II. Libraries of Compounds

In another aspect, the invention provides libraries of compounds of Formula I. Libraries of the invention are useful, e.g., for drug discovery. For example, a library of the invention can be screened (e.g., according to the methods described herein) to determine whether the library includes compounds having a pre-selected activity. Thus, for example, a library can be screened to determine whether compounds of the library have SH3 domain binding activity or any other activity which can be detected in vitro or in vivo, e.g., anti-inflammatory activity, cell growth stimulatory activity, anti-neoplastic activity, and the like.

The synthesis of combinatorial libraries is well known in the art and has been reviewed (see, e.g., E. M. Gordon et al., *J. Med. Chem.* 37:1385–1401 (1994)). Thus, the subject invention contemplates methods for synthesis of combinatorial libraries of compounds of Formula I. Such libraries can be synthesized according to a variety of methods. For example, a "split-pool" strategy can be implemented in the following way: beads of a functionalized polymeric support (such as Wang resin) are placed in a plurality of reaction vessels. To each aliquot of beads is added a solution of an N-Boc protected amino acid, and a coupling reagent (e.g., DCC) is added to each vessel. The reactions are allowed to proceed to yield a plurality of immobilized amino acids. The aliquots of derivatized beads are then washed, "pooled" (i.e., recombined), the N-Boc protecting group is removed (e.g., with a solution of TFA in DCM) and the pool of beads is again divided, with each aliquot being placed in a separate reaction vessel. To each reaction vessel is added a solution of an aldehyde (e.g., an aldehyde such as compound 6 of Scheme 1) and a reducing agent such as sodium cyanoborohydride, and reductive amination occurs to yield a plurality of reaction vessels each containing a plurality of compounds immobilized on solid support. The immobilized compounds can be cyclized, e.g., as shown in Scheme 1, by deprotection and intramolecular lactamization, to provide a library of compounds of Formula I (in which $R_2$ is —$C(R_{2a})(R_{2b})C(O)R_5$). The library of immobilized compounds can then be washed to remove impurities. In certain embodiments, the library of compounds can be further treated, e.g., by deprotection and derivatization of the amino functionality. Further processing can optionally include cleavage from the solid support, if desired, and further reaction (e.g., substitution or further functionalization).

In another illustrative method of combinatorial synthesis, a "diversomer library" is created by a modification of the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., Nature 354:84–86 (1991)) can also be used to synthesize libraries of compounds according to the subject invention.

For examples of combinatorial library synthesis, see Examples 6 and 9, infra.

Combinatorial libraries can be screened to determine whether any members of the library have a desired activity, and, if so, to identify the active species. Methods of screening combinatorial libraries have been described (see, e.g., Gordon et al., *J. Med. Chem.*, op. cit.). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assay formats useful for screening the libraries of the invention are known in the art (see, e.g., E. M. Gordon et al., *J. Med. Chem.* 37:1385–1401 (1994)). See also Example 12, infra.

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 2 compounds, more preferably at least about 30 compounds, more preferably at least about 100 compounds, more preferably at least about 500 compounds, and still more preferably at least about 1000 compounds. In certain embodiments, the libraries of the invention can include at lest $10^4$ compounds, $10^5$ compounds, $10^6$ compounds, or $10^7$ compounds. However, in certain preferred embodiments, the libraries of compounds of the invention contain fewer than $10^9$ compounds, more preferably fewer than $10^8$ compounds, and still more preferably fewer than $10^7$ compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably at least about 90%, and most preferably at least about 95%.

The libraries of the invention can be prepared according to the methods described herein, or by other synthetic methods which will be apparent to the ordinarily-skilled artisan. In general, such methods will involve the preparation of libraries by providing variegated populations of amino acids or of the 5,6-spirolactams of the invention. The term "variegated population", as used herein, refers to a population including at least two different chemical entities, e.g., of different chemical structure. For example, a "variegated population" of amino acids would comprise at least two different amino acids. Similarly, a variegated population of spirolactams comprises at least two different spirolactams.

III. Pharmaceutical Compositions

In another aspect, the invention provides pharmaceutical compositions comprising a compound of the invention, or a pharmaceutically-acceptable salt thereof, and a pharmaceutically-acceptable carrier.

The pharmaceutical compositions of the invention comprise a therapeutically-effective amount of one or more of the compounds described above (e.g., Compounds of Formula I, including Formula Ia), formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect, e.g., treating (i.e., preventing or ameliorating) cancer in a subject, or inhibiting protein-protein interactions mediated by an SH3 domain in a subject, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds can contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (See, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound of the invention in the proper medium. Absorption enhancers can also be used to increase the flux of the compound of the invention across the skin. The rate of such flux can be controlled by either providing a rate controlling membrane or dispersing the compound of the invention in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral or topical administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the derivative (e.g., ester, salt or amide) thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient, when used for the indicated effects, will range from about 0.0001 to about 100 mg per kilogram of body weight per day, more preferably from about 0.01 to about 50 mg per kg per day, and still more preferably from about 0.1 to about 40 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

IV. Methods of Modulating Interactions Mediated by SH3 Domains

In still another aspect, the invention provides methods for modulating an activity mediated by an SH3 domain. In general, the methods include the step of contacting an SH3 domain with a compound of the invention, such that activity of the SH3 domain is modulated.

The methods of the invention provide means for inhibiting protein-protein interactions mediated by SH3 domains. Proteins with SH3 domains couple protein-tyrosine kinases to signalling networks involved in growth regulation (see, e.g., Smithgall, op cit. and references cited therein). Disruption of growth-regulatory signal transduction can result in inhibition of cell growth. Accordingly, the invention provides methods for inhibiting growth of cells, including microbial cells and transformed cells, e.g., by inhibiting protein-protein interactions mediated by SH3 domains involved in growth-regulatory signal transduction. Thus, the invention provides methods for treating conditions associated with abnormal or undesired cell growth, including, e.g., fungal or bacterial infections, neoplastic conditions (including cancer), and the like.

In one embodiment, the invention provides a method for modulating intracellular signaling pathways by disrupting particular protein-protein interactions mediated by SH3 domains. For instance, the SH3 inhibitors of the present invention can be used to affect the responsiveness of a cell to a growth factor, cytokine or other receptor ligand, and to inhibit the proliferation of transformed cells or to render transformed cells more sensitive to cytostatic or cytotoxic agents. The SH3 target of the subject inhibitors can range from the interaction between, for example, an activated receptor complex and the initial cytoplasmic proteins involved in triggering a particular set of intracellular signaling pathways, to the last SH3-mediated interaction in a specific pathway, such as the formation of a transcription factor complex or allosteric regulation of an enzymatic activity. Thus, the inhibitors of the present invention can be used to inhibit the interaction between an SH3-binding signal transduction protein such as Grb2, and such SH3-containing proteins as, for example, Src, p85, Fyn, Lyn, Hck, Syk, Grb2, Gap, STAT, p47-phox, p67-phox, Btk, and the like.

Interaction with SH3 domains can lead to activation of the biochemical function associated with the target protein. Examples of this phenomenon include the microtubule-associated GTPase, dynamin Gout et al., 1993) as well as PI-3K (Pleiman et al., 1994) In the case of PI-3K, binding of the SH3 domains of the Src-related kinases Fyn and Lyn significantly increased PI-3K enzymatic activity (Pleiman et al., 1994). This event may have biological relevance in B-cells, in which occupation of the B-cell receptor with antigen leads to activation of Lyn and its association with the p85 subunit of PI-3K. Introduction of p85-based prolinie-rich peptides into permeabilized B-cells completely blocked antigen receptor-mediated activation of PI-3K (Pleiman et al., 1994). This result suggests that the Lyn SH3-p85 interaction is required for PI-3K activation in intact cells. Thus, analogs based on the target motif in this case (p85 subunit) can inhibit protein-protein interaction and activation of the downstream effector.

In a preferred embodiment, the methods of the invention for inhibition of protein-protein interactions mediated by SH3 domains include the step of contacting an SH3 domain with a compound of Formula I, more preferably a compound of Formula Ia. In preferred embodiments, the compound is selected to preferentially inhibit an SH3 domain of an abnormal cell (such as a cancer cell), or a pathogen cell (e.g., a fungal pathogen). Thus, in preferred embodiments, the methods of the invention comprise contacting an SH3 domain of a target protein with a compound of the invention which is selective for the target protein SH3 domain.

Compounds useful in the methods of the invention can be determined by the skilled artisan in light of the teaching herein using no more than routine experimentation. For example, example 12, infra, provides an assay for compounds that inhibit an interaction between a natural peptide ligand and an SH3 domain. Thus, the assay of Example 12 provides a rapid, high-throughput screening system for identifying compounds useful for inhibiting protein-protein interactions mediated by SH3 domains. A similar assay, using an SH3 domain of a non-target protein, can be used to determine the selectivity of a given compound of the invention for a target protein in preference to a non-target protein. Other assays which measure the ability of a compound to inhibit proliferation, to alter the responsiveness of a cell to a growth factor, and the like, will be apparent to the ordinarily-skilled artisan. For example, the ability of a compound of the invention to inhibit cell growth in culture can be measured by standard assays.

REFERENCES

1. Cohen, G. B., Ren, R. and Baltimore, D. (1995) Cell 80, 237–248
2. Pawson, T. (1995) Nature 373, 573–580
3. Vihinen, M. and Smith, C. I. E. (1996) Crit Rev Immunol 16, 251–275
4. Kuriyan, J. and Cowburn, D. (1993) Current Opinion in Structural Biology 3, 828–837
5. Viguera, A. R., Jim,nez, M. A., Rico, M. and Serrano, L. (1996) Journal of Molecular Biology 255, 507–521
6. Grzesiek, S., Bax, A., Clore, G. M., Gronenborn, A. M., Hu, J. S., Kaufman, J., Palmer, I., Stahl, S. J. and Wingf~eld, P. T. (1996) Nature Structural Biology 3, 340–345 Gorina, S. and Pavletich, N. P. (1996) Science 274, 1001–1005
7. Gorina, S. and Pavletich, N.P. (1996) Science 274, 1001–1005.
8. Yu, H., K., C. J., Feng, S., Dalgarno, D. C., Braurer, A. W. and Schreiber, S. L. (1993) Cell 76, 933–945
9. Feng, S., Chen, J. K., Yu, H., Simon, J. A. and Schreiber, S. L. (1994) Science 266, 1241–1247
10. Goudreau, N., Cornille, M., Duchesne, M., Parker, F., Tocque, B., Garbay, C. and Roques, B. P. (1994) Nature Structural Biology 1, 898–907
11. Lim, W. A., Richards, F. M. and Fox, R. O. (1994) Nature 372, 375–379
12. Wu, X., Knudsen, B., Felller, S. M., Zheng, J., Sali, A., Cowburn, D., Hanafusa, H. and Kuriyan, J. (1995) Structure 3, 215–226
13. Terasawa, H., Kohda, D., Hatanaka, H., Tsuchiya, S., Ogura, K., Nagata, K., Ishii, S., Mandiyan, V., Ullrich, A., Schlessinger, J. and Inagaki, F. (1994) Nature Structural Biology 1, 891–897
14. Wittekind, M., Mapelli, C., Farmer II, B. T., Suen, K.-L., Goldfarb, V., Tsao, J., Lavoie, T., Barbacid, M., Meyers, C. A. and Mueller, L. (1994) Biochemistry 33, 13531–13539
15. Musacchio, A., Saraste, M. and Wilmanns, M. (1994) Nature Structural Biology 1, 546–551
16. Lee, C.-H., Saksela, K., Mirza, U. A., Chait, B. T. and Kuriyan, J. (1996) Cell 85, 931–942
17. Feng, S., Kapoor, T. M., Shirai, F., Combs, A. P. and Schreiber, S. L. (1996) Chemistry & Biology 3, 661–670
18. Renzoni, D. A., Pugh, D. J. R., Siligardi, G., Das, P., Morton, C. J., Rossi, C., Waterfield, M. D., Campbell, I. D. and Ladbury, J. E. (1996) Biochemistry 35, 15646–15653
19. Kahn, M. g. e. S. (1993) Tetrahedron, 3433–3677
20. Doyle, P. M., Harris, J. C., Moody, C. M., Sadler, P. J., Sims, M., Thornton, J. M., Uppenbrink, J. and Viles, J. H. (1996) Int J Pept Protein Res 47, 427–436
21. Haubner, R., Schmitt, W., Hoelzemarin, G., Goodman, S. L., Jonczyk, A. and Kessler, H. (1996) J Am Chem Soc 118, 7881–7891
22. Prasad, S., Rao, R. B., Bergstrand, H., Lundquist, B., Becker, E. L. and Balaram, P. (1996) Int J Pept Protein Res 48, 312–318
23. Reich, V., Mostov, K. and Aroeti, B. (1996) J Cell Sci 109, 2133–2139
24. Virgilio, A. A., Schuerer, S. C. and Ellman, J. A. (1996) Tetrahedron Lett 37, 6961–6964
25. Ramakrishnan, C., Srinivasan, N. and Nataraj, D. V. (1996) Int J Pept Protein Res 48, 420–428
26. Hartzoulakis, B., Rutherford, T. J., Ryan, M. D. and Gani, D. (1996) Tetrahedron Lett 37, 6911–6914
27. Olsen, G. L., Bolin, D. R., Bonner, M. P., Bos, M., Cook, C. M., Fry, D. C., Graves, B. J., Hatada, M., Hill, D. E., Kahn, M., Madison, V. S., Rusiecki, V. K., Sarabu, R., Sepinwall, J., Vincent, G. P. and Voss, M. E. (1993) Journal of Medicinal Chemistry 36, 3039–3055
28. Giannis, A. and Kolter, T. (1993) Angew. Chem. Int. Ed. Engl. 32, 1244–1267
29. Schreiber, S. et al. J. Am. Chem. Soc. 1998, 120, 30.

EXEMPLIFICATION

Materials and Methods

In the Examples, all temperatures are in degrees Centigrade (° C.). Melting points are uncorrected and were determined on a Mel-Temp II (Laboratory Devices, USA) using open capillary tubes. Infrared spectra (IR) were recorded on a Perkin-Elmer Spectrum 1000. Mass spectra (MS) were recorded on a Platform 2 Micromass instrument. Nuclear magnetic resonance (NMR) spectra were measured on a Varian 200 instrument in the specified solvent with tetramethylsilane (TMS) as internal standard for $^1$H NMR. For $^{13}$C NMR spectra, the deuterated solvent peak was used as the reference with its position set relative to TMS.

Where possible all reactions were followed by thin layer chromatography (TLC) and visualized using UV fluorescence, 3% $KMnO_4$ (aqueous) staining, and/or dodecamolybdophosphoric acid. Commercial thin layer and preparative layer chromatography plates were Si250F and Si500F, respectively, from J. T. Baker. Flash chromatography was performed using 40 μm "Baker" silica gel from J. T. Baker. All solvent mixtures are listed as volume ratios.

Abbreviations: EDCI: 1-(3-dimethylaminopropyl)-ethylcarbodiimide; EtOAc, ethyl acetate; BOP: benzotriazol-1-yl-oxy-tris(dimethylamino)phosphonium hexafluorophosphate; HOBt: 1-hydroxybenzotriazole; NMM: N-methylmorpholine

EXAMPLE 1

Synthesis of Spirolactams

In an exemplary synthesis, the spirolactam was preformed to generate the N- and C-terminus suitably protected for subsequent library formation. Initially, commercially available tert-butyl proline ester (2) is protected as the Cbz-amide 3 (Scheme 1). Alkylation with allylic bromide to olefin 4, followed by hydroboration/oxidation delivers the alcohol 5. Swern oxidization gives the aldehyde 6. Alternatively, alkylation with homoallylic bromide can be followed by oxidative cleavage to the aldehyde; this was found to result in a somewhat reduced yield. Reductive alkylation with glycine methyl ester affords amine 7 together with dialkylated amine, which are easily separable by chromatography. Trifluoroacetic acid (TFA) deprotection generates the amino acid 8, which can then be cyclized to provide a compound of Formula I (1). As shown in scheme 1, this compound can be selectively deprotected at either terminus to permit further modifications, for generation of additional compounds of the invention.

Scheme 1

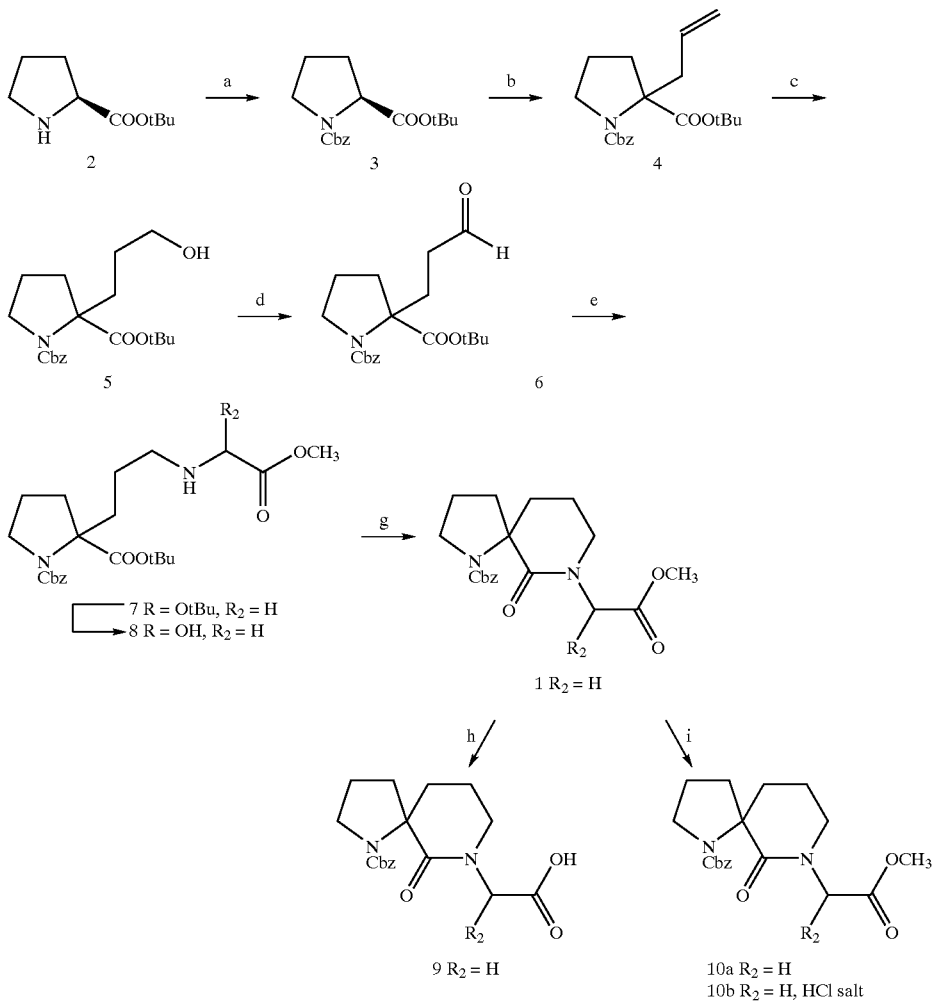

<sup>a</sup>Reagents: (a) CbzCl, DIPEA (80%); (b) LDA, Allyl bromide, (65%); (c) i) BH$_3$•THF ii) KOH/H$_2$O$_2$ (90%); (d) Swern oxid. (90%); (e) Gly•HCl, DIPEA, MeOH, then NaBH$_4$ (78%); (f) TFA/CH$_2$Cl$_2$ (g) EDCI, NMM (90%); (h) KOH (aq) (95%); (i) H$_2$, Pd(OH)$_2$/C (94%)

In the initial reaction sequence the carboxylic acid of proline was protected as a methyl ester. However, cyclization or hydrolysis of the ester could not readily be achieved. The tert-butyl ester alleviated the difficulty. In the presence of EDCI, the amino acid cyclizes to spirolactam 1.

EXAMPLE 2

Synthesis of a Spirolactam Library

In an illustrative synthesis, a spirolactam library was constructed by functionalizing the N- and C-terminus as shown in Scheme 2. The Cbz-protected spirolactam was extended in the C-terminal direction by activation with N-hydroxysuccinimide and subsequent coupling with various nucleophiles such as amines. Library synthesis was conducted in 96-well microtiter plates. A stock solution of the carboxyl-activated spirolactam was added to each well containing a solution of an amine (1° and 2° amine, amino acid, or peptide). After the reactions were complete as determined by TLC, each well was washed with H$_2$O. The organic fractions were concentrated to yield a plate of respective amides (e.g. 11, R$_1$=Cbz, R$_2$=H, R$_3$=benzyl amine). To extend the diversity in the library the functionality in the N-terminal direction was varied. The amine is deprotected by hydrogenolysis to yield 10 (Scheme 1). The amine was converted to ureas, amides, or sulfonamides (Table 2) (e.g., compound 12, Example 7, R$_1$=2'-methylphenyl urea, R$_2$=H, R$_3$=OCH$_3$; compound 13, Example 8, R$_1$=Boc-Leu, R$_2$=H, R$_3$=OCH$_3$). Hydrolysis of the methyl esters with 1 N KOH generated the free acids, which were activated with N-hydroxysuccinimide or isobutyl chloroformate, and coupled to a collection of amines to yield compounds of Formula 1. The use of isobutylchloroformate generates a mixed anhydride, thus allowing the use of alcohols to yield esters. The work-up procedure is simplified, since the by-products of the reaction can simply be evaporated away from the desired material.

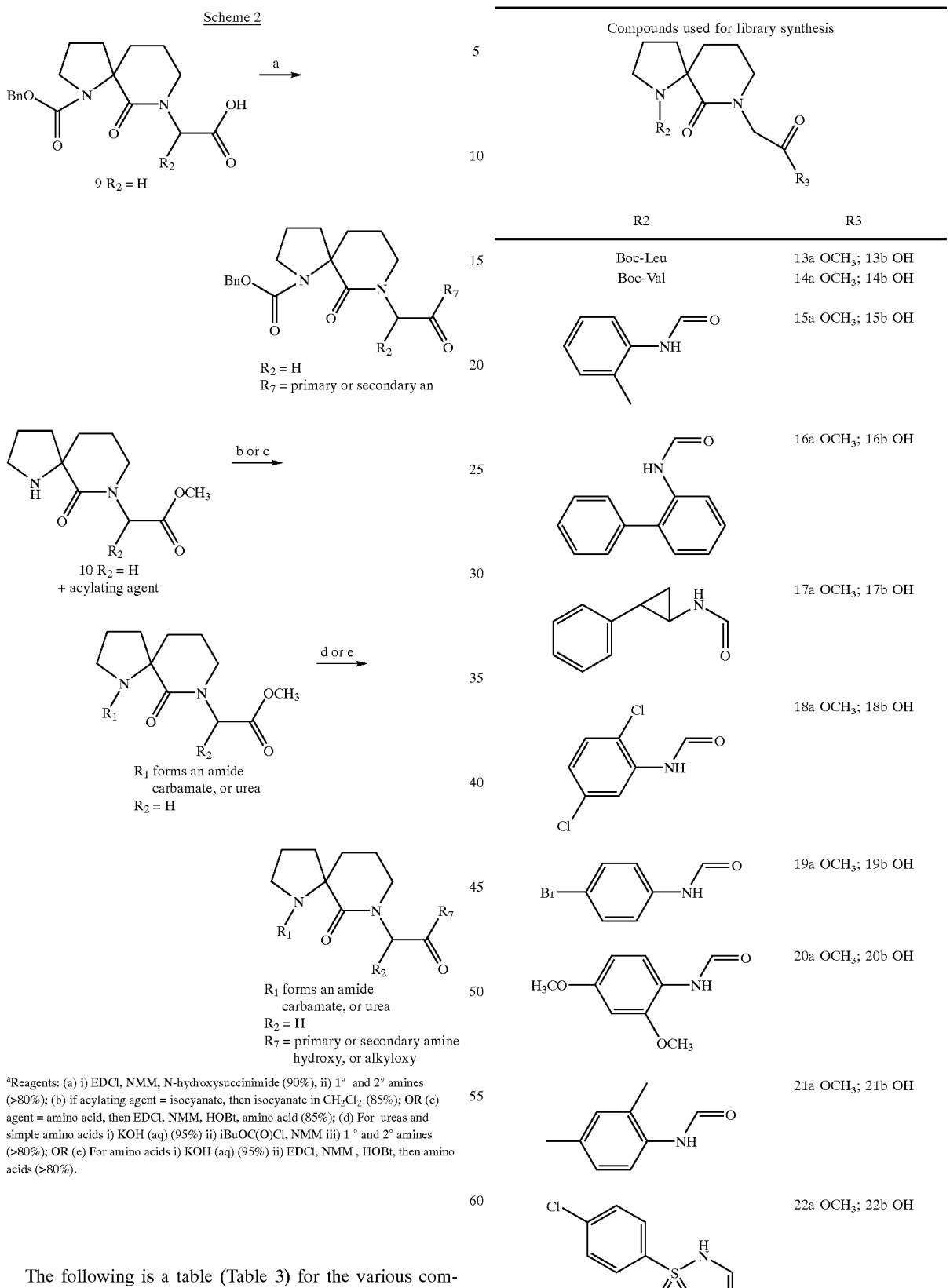
The following is a table (Table 3) for the various compounds used as starting materials for the libraries. Both the methyl ester and the free acids are listed. However, only the free acids were used as starting materials for the libraries.

TABLE 3-continued

Compounds used for library synthesis

| R2 | R3 |
|---|---|
| (4-acetylphenyl)-NH-CHO | 23a OCH$_3$; 23b OH |
| 2-methylphenyl-SO$_2$-NH-CHO | 24a OCH$_3$; 24b OH |
| 1-adamantyl-NH-CHO | 25a OCH$_3$; 25b OH |
| 4-methylphenyl-SO$_2$- | 26a OCH$_3$; 26b OH |
| cyclohexyl-NH-CHO | 27a OCH$_3$; 27b OH |
| tert-octyl-NH-CHO | 28a OCH$_3$; 28b OH |

N-Terminus Modifications (Methyl Esters):

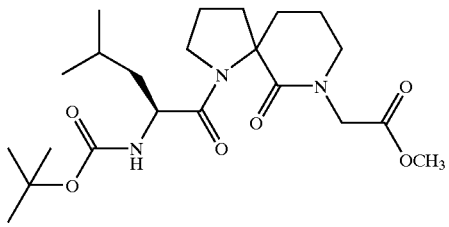

General Procedure for Methyl Spirocyclic Dipeptide Ester (13a). To a cooled solution 0° C. of crude spirocyclic methyl ester 10a (91.1 mg, 403 mmol), N-Boc-Leu-OH·H$_2$O (201 mg, 806 mmol), and HOBt (82 mg, 605 mmol) in DMF (4 mL) was added NMM (66 mL, 605 mmol), then EDCI (116 mg, 605 mmol). The reaction mixture was allowed to warm to room temperature. After 24 h, the solvent volume was removed in vacuo, and the residue was purified by flash chromatography (SiO$_2$; 100% EtOAc, R$_f$ 0.30) to yield a white solid (124 mg, 69.8%):

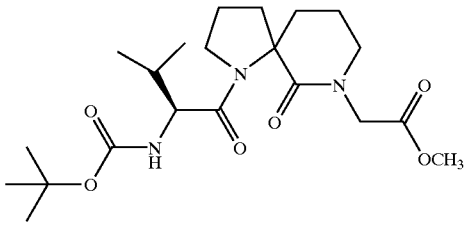

(14a). The same method as for the preparation of dipeptide 13a was employed. Thus, coupling of crude spirocyclic methyl ester 10a (400 mg, 1.52 mmol) with N-Boc-Val-OH (662 mg, 3.04 mmol) afforded 14a as a hydroscopic solid (347 mg, 53.5% over 4 steps) after flash chromatography (SiO$_2$; 100% EtOAc, R$_f$ 0.25): IR (CH$_2$Cl$_2$ cast) 3300 (br w), 2965 (m), 2873 (w), 1750 (m), 1707 (s), 1636 (s) cm$^1$; $^1$H NMR (200 MHz, CDCl$_3$) d 5.02–5.29 (m, 1H), 4.49 & 4.46 (d, 1H, J=17.2 Hz), 4.08–4.30 (m, 1H), 3.35–3.85 (m, 6H), 3.02–3.18 (m, 1H), 2.77 (d, 1H, J=18.0 Hz), 2.30–2.51 (m, 1H), 1.64–2.30 (m, 7H), 1.40–1.64 (m, 1H), 1.27 (br s, 9H, C(CH$_3$)$_3$), 0.66–0.92 (m, 6H, (CH$_3$)$_2$); $^{13}$C NMR (50 MHz, CDCl$_3$) many peaks, contained peaks for rotomers of diastereomers.

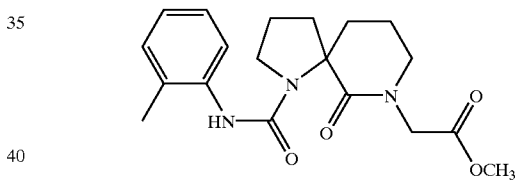

General Procedure for Methyl Spirocyclic Urea Ester (15a). To a solution of crude spirocyclic methyl ester hydrochloride 10b (400 mg, 1.52 mmol) and DIPEA (398 mL, 2.28 mmol) in CH$_2$Cl$_2$ (15 mL) was added 2-methylphenylisocyanate (208 mL, 1.67 mmol). The reaction mixture was stirred at RT for 3 d. The solvent volume was removed in vacuo, and the residue was purified by flash chromatography (SiO$_2$; 100% EtOAc, R$_f$ 0.35) to yield a white solid (298 mg, 54.6% over 4 steps): mp 169–171° C.; IR (CH$_2$Cl$_2$ cast) 3318 (br w), 2950 (w), 2868 (w), 1748 (m), 1638 (s) cm$^1$; $^1$H NMR (200 MHz, CDCl$_3$) d 7.60 (br d, 1H, J=7.8 Hz, Ar—H), 7.02–7.16 (m, 2H, Ar—H), 6.91 (br dd, 1H, J=7.8, 7.2 Hz, Ar—H), 6.14 (br s, 1H, NH), 4.69 & 4.70 (d, 1H, J=17.2 Hz, 1×a-gly-CH$_2$), 3.64 & 3.66 (s, 3H, OCH$_3$), 3.42–3.64 (m, 3H), 3.41 & 3.61 (d, 1H, J=17.2 Hz, 1×a-gly-CH$_2$), 3.12–3.26 (m, 1H), 2.60–2.78 (m, 1H), 2.14–2.36 (m, 1H), 2.17 & 2.18 (s, 3H, CH$_3$), 1.77–2.14 (m, 5H), 1.62–1.77 (br d, 1H, J=12.8 Hz); $^{13}$C NMR (50 MHz, CDCl$_3$) d 172.99, 169.96, 153.65, 136.90, 130.04, 128.83, 126.38, 123.65, 122.89, 65.94, 51.77, 48.66, 48.60, 47.63, 37.99, 32.58, 23.41, 21.24, 17.57.

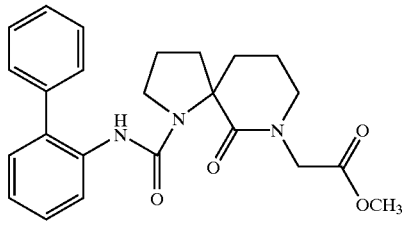

The same method as for the preparation of 15a was employed. Thus, acylation of crude spirocyclic methyl ester hydrochloride 10b (465 mg, 1.77 mmol) with isocyanate (334 mL; 1.95 mmol)) in $CH_2Cl_2$ (20 mL) afforded 16a as a white solid (400 mg, 53.6% over 4 steps) after flash chromatography ($SiO_2$; 100% EtOAc, $R_f$0.25): mp 149–151° C.; IR ($CH_2Cl_2$ cast) 3433 (w), 2950 (w), 2868 (w), 1748 (m), 1648 (s) $cm^{-1}$; $^1$H NMR (200 MHz, $CDCl_3$) d 8.14 (br d, 1H, J=8.2 Hz, Ar—H), 7.34–7.52 (m, 5H, Ar—H), 7.28 (ddd, 1H, J=7.5, 7.4, 1.0 Hz, Ar—H), 7.14 (dd, 1H, J=7.5, 1.0 Hz, Ar—H), 7.04 (dd, 1H, J=7.6, 7.5 Hz, Ar—H), 6.43 (br s, 1H, NH), 4.80 (d, 1H, J=17.5 Hz, 1×a-gly-$CH_2$), 3.71 (s, 3H, $OCH_3$), 3.52–3.72 (m, 1H), 3.48 (d, 1H, J=17.5 Hz, 1×a-gly-$CH_2$), 3.15–3.32 (m, 2H), 3.00–3.15 (m, 1H), 2.72 (ddd, 1H, J=12.4, 12.4, 5.2 Hz), 2.18–2.38 (m, 1H), 1.80–2.10 (m, 5H), 1.70 (br d, 1H, J=13.0 Hz); $^{13}$C NMR (50 MHz, $CDCl_3$) d 173.08, 170.13, 153.33, 138.66, 136.14, 131.29, 129.62, 129.42; 129.12, 128.40, 127.87, 122.56, 120.05, 66.02, 51.98, 48.80, 48.73, 47.31, 38.07, 32.65, 23.49, 21.41.

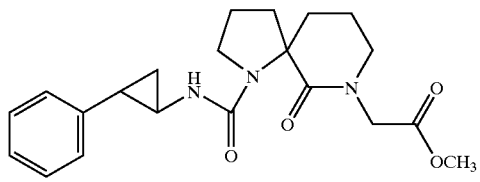

The same method as for the preparation of 15a was employed. Thius, acylation of crude spirocyclic methyl ester hydrochloride 10b (465 mg, 1.77 mmol) with isocyanate (289 mL; 1.95 mmol)) in $CH_2Cl_2$ (20 mL) afforded 17a as a tacky solid (442 mg, 64.8% over 4 steps) after flash chromatography ($SiO_2$; 100% EtOAc, $R_f$0.25–0.18): Note: the combined material contains both isomers of 90% trans-cyclopropyl spirolactam and both isomers of 10% cis-cyclopropyl spirolactam. IR ($CH_2Cl_2$ cast) 3422 (br w), 2950 (w), 2869 (w), 1748 (m), 1631 (br s) $cm^{-1}$; $^1$H NMR (200 MHz, $CDCl_3$) d 6.93–7.22 (m, 5H, Ar—H), 5.13 & 5.27 (br s, 1H), 5.21 (d, 0.5H, J=2.2 Hz), 4.45–4.74 (m, 1H), 3.63 & 3.64 (s, 3H, $OCH_3$), 3.22–3.62 (m, 3.5H), 3.05–3.22 (m, 1H), 2.71–2.86 (m, 1H), 2.47–2.71 (m, 1H), 2.02–2.27 (m, 1H), 1.52–2.02 (m, 5H), 0.94–1.24 (m, 3H); $^{13}$C NMR (50 MHz, $CDCl_3$) d 173.16, 173.13, 169.76, 158.93, 156.58, 156.49, 141.18, 141.12, 140.57, 128.04, 127.86, 125.81, 125.73, 125.60, 125.34, 125.31, 65.41, 65.36, 53.23, 51.60, 48.51, 48.42, 47.22, 47.07, 37.96, 37.64, 34.38, 32.79, 32.33, 24.82, 24.17, 23.55, 23.17, 23.08, 21.03, 17.47, 16.69, 16.28, 15.22.

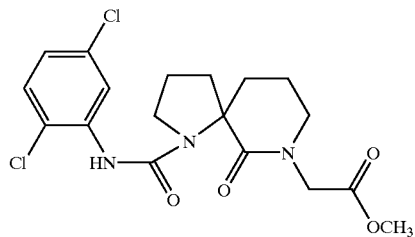

The same method as for the preparation of 15a was employed. Thus, acylation of crude spirocyclic methyl ester hydrochloride 10b (465 mg, 1.77 mmol) with isocyanate (367 mg; 1.95 mmol)) in $CH_2Cl_2$ (20 mL) afforded 18a as a white solid (351 mg, 47.8%over 4 steps) after flash chromatography ($SiO_2$; 100% EtOAc, $R_f$0.25): mp 193–194° C.; IR ($CH_2Cl_2$ cast) 3428 (w), 2949 (w), 2857 (w), 1742 (s), 1676 (m), 1644 (s) $cm^{-1}$; $_1$H NMR (200 MHz, $CDCl_3$) d 8.32 (d, 1H, J=2.6 Hz, Ar—H), 7.19 (d, 1H, J=8.8 Hz, Ar—H), 6.89 (br s, 1H, NH), 6.86 (dd, 1H, J=8.8, 2.6 Hz, Ar—H), 4.69 (d, 1H, J=17.5 Hz, 1×a-gly-$CH_2$), 3.71 (s, 3H, $OCH_3$), 3.54–3.74 (m, 3H), 3.60 (d, 1H, J=17.5 Hz, 1×a-gly-$CH_2$), 3.21–3.33 (m, 1H), 2.72 (ddd, 1H, J=12.6, 12.2, 5.4 Hz), 2.21–2.44 (m, 1H), 1.82–2.23 (m, 5H), 1.74 (br d, 1H, J=12.8 Hz); $^{13}$C NMR (50 MHz, $CDCl_3$) d 172.72, 169.91, 152.25, 136.72, 133.41, 129.21, 122.64, 120.15, 119.77, 66.29, 52.00, 48.80, 48.80, 47.78, 38.16, 32.33, 23.46, 21.24.

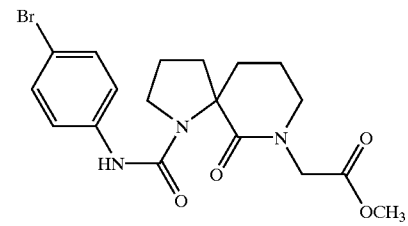

The same method as for the preparation of 15a was employed. Thus, acylation of crude spirocyclic methyl ester hydrochloride 10b (465 mg, 1.77 mmol) with isocyanate (386 mg; 1.95 mmol)) in $CH_2Cl_2$ (20 mL) afforded 19a as a white solid (399 mg, 53.1% over 4 steps) after flash chromatography ($SiO_2$; 100% EtOAc, $R_f$0.23): mp 185–187° C.; IR ($CH_2Cl_2$ cast) 3332 (br w), 2952 (w), 2869 (w), 1749 (m), 1638 (s), 1591 (m) $cm^{-1}$; $^1$H NMR (200 MHz, $CDCl_3$) d 7.31 (d, 2H, J=9.6 Hz, Ar—H), 7.25 (d, 2H, J=9.6 Hz, Ar—H), 6.58 (br s, 1H, NH), 4.69 (br d, 1H, J=17.2 Hz, 1×a-gly-$CH_2$), 3.72 (s, 3H, $OCH_3$), 3.48–3.68 (m, 3H), 3.20–3.33 (m, 1H), 2.72 (br ddd, 1H, J=12.4, 12.2, 5.6 Hz), 2.14–2.37 (m, 1H), 1.80–2.12 (m, 5H), 1.73 (br d, 1H, J=13.0 Hz); $^{13}$C NMR (50 MHz, $CDCl_3$) d 173.11, 170.08, 153.27, 138.39, 131.62, 121.48, 115.13, 66.15, 52.07, 48.89, 48.89, 47.87, 38.16, 32.47, 23.52, 21.35.

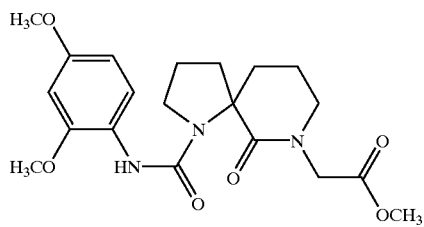

The same method as for the preparation of 15a was employed. Thus, acylation of crude spirocyclic methyl ester hydrochloride 10b (465 mg, 1.77 mmol) with isocyanate (349 mg; 1.95 mmol)) in CH$_2$Cl$_2$ (20 mL) afforded 20a as a white solid (406 mg, 56.6% over 4 steps) after flash chromatography (SiO$_2$; 100% EtOAc, R$_f$ 0.23): mp 144–145° C.; IR (CH$_2$Cl$_2$ cast) 3441 (w), 2949 (w), 2867 (w), 1748 (m), 1649 (s), 1617 (m) cm$^{-1}$; $^1$H NMR (200 MHz, CDCl$_3$) d 7.88 (br d, 1H, J=8.6 Hz, Ar—H), 6.62 (br s, 1H, NH), 6.39 (d, 1H, J=2.4 Hz, Ar—H), 6.38 (dd, 1H, J=8.6, 2.4 Hz, Ar—H), 4.78 (d, 1H, J=17.2 Hz, 1xa-gly-CH$_2$), 3.78 (s, 3H, OCH$_3$), 3.72 (s, 3H, OCH$_3$), 3.69 (s, 3H, OCH$_3$), 3.50–3.75 (m, 3H), 3.46 (d, 1H, J=17.2 Hz, 1xa-gly-CH$_2$), 3.18–3.29 (m, 1H), 2.74 (ddd, 1H, J=12.8, 12.4, 4.6 Hz), 2.20–2.39 (m, 1H), 1.80–2.20 (m, 5H), 1.71 (br d, 1H, J=12.8 Hz); $^{13}$C NMR (50 MHz, CDCl$_3$) d 173.22, 170.13, 155.24, 153.50, 148.96, 122.30, 120.29, 103.81, 98.38, 65.91, 55.64, 55.47, 51.91, 48.76, 48.67, 47.63, 38.25, 32.71, 23.49, 21.39.

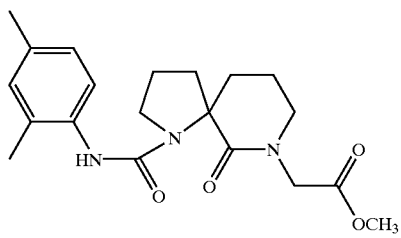

The same method as for the preparation of 15a was employed. Thus, acylation of crude spirocyclic methyl ester hydrochloride 10b (465 mg, 1.77 mmol) with isocyanate (275 mL; 1.95 mmol)) in CH$_2$Cl$_2$ (20 mL) afforded 21a as a white solid (385 mg, 58.2% over 4 steps) after flash chromatography (SiO$_2$; 100% EtOAc, R$_f$ 0.28): mp 134–135° C.; IR (CH$_2$Cl$_2$ cast) 3312 (br w), 2951 (w), 2860 (w), 1748 (m), 1637 (s), 1589 (m) cm$^{-1}$; $^1$H NMR (200 MHz, CDCl$_3$) d 7.46 (d, 1H, J=8.8 Hz, Ar—H), 6.87–6.97 (m, 2H, Ar—H), 5.98 (br s, 1H, NH), 4.74 (d, 1H, J=17.4 Hz, 1xa-gly-CH$_2$), 3.69 (s, 3H, OCH$_3$), 3.48–3.74 (m, 3H), 3.44 (d, 1H, J=17.4 Hz, 1xa-gly-CH$_2$), 3.15–3.29 (m, 1H), 2.73 (ddd, 1H, J=12.4, 12.4, 5.2 Hz), 2.23 (s, 3H, CH$_3$), 2.18 (s, 3H, CH$_3$), 1.81–2.38 (m, 6H), 1.74 (br d, 1H, J=13.0 Hz); $^{13}$C NMR (50 MHz, CDCl$_3$) d 173.24, 170.19, 154.09, 134.29, 133.59, 130.92, 129.42, 127.18, 123.53, 66.11, 51.95, 48.84, 48.76, 47.79, 38.22, 32.85, 23.61, 21.46, 20.70, 17.71.

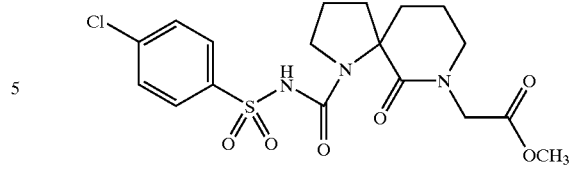

The same method as for the preparation of 15a was employed. Thus, acylation of crude spirocyclic methyl ester hydrochloride 10b (465 mg, 1.77 mmol) with isocyanate (343 mL; 1.95 mmol)) in CH$_2$Cl$_2$ (20 mL) afforded 22a as a white solid (546 mg, 69.5% over 4 steps) after flash chromatography (SiO$_2$; 1/9 MeOH/EtOAc, R$_f$ 0.20): mp 135–145° C. (softens at 84–90° C.); IR (CH$_2$Cl$_2$ cast) 3333 (br w), 2953 (w), 2877 (w) 1748 (m), 1670 (m), 1651 (s), 1635 (s) cm$^{-1}$; $^1$H NMR (200 MHz, CDCl$_3$) d 7.78–8.03 (m, 2H, Ar—H), 7.28 & 7.36 (d, 2H, J=8.0 Hz, Ar—H), 3.95–4.28 (m, 1H), 3.66 (br s, 3H, OCH$_3$), 3.35–3.95 (m, 4H), 3.05–3.24 (m, 1H), 2.34–2.60 (m, 1H), 2.06–2.30 (m, 1H), 1.70–2.06 (m, 5H), 1.50–1.70 (m, 1H); $^{13}$C NMR (50 MHz, CDCl$_3$) d peaks were not resolved.

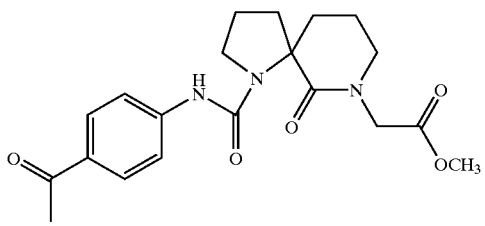

The same method as for the preparation of 15a was employed. Thus, acylation of crude spirocyclic methyl ester hydrochloride 10b (465 mg, 1.77 mmol) with isocyanate (314 mg; 1.95 mmol)) in CH$_2$Cl$_2$ (20 mL) afforded 23a as a white solid (431 mg, 62.8% over 4 steps) after flash chromatography (SiO$_2$; 100% EtOAc, R$_f$ 0.17): mp 161–163° C.; IR (CH$_2$Cl$_2$ cast) 3329 (br w), 2950 (w), 1748 (m), 1654 (br s), 1587 (m) cm$^{-1}$; $^1$H NMR (200 MHz, CDCl$_3$) d 7.77 (d, 2H, J=8.8 Hz, Ar—H), 7.43 (d, 2H, J=8.8 Hz, Ar—H), 7.18 (br s, 1H, NH), 4.64 (d, 1H, J=17.5 Hz, 1xa-gly-CH$_2$), 3.68 (s, 3H, OCH$_3$), 3.48–3.72 (m, 4H), 3.17–3.31 (m, 1H), 2.70 (ddd, 1H, J=12.4, 12.4, 5.2 Hz), 2.47 (s, 3H, CH$_3$), 2.07–2.29 (m, 1H), 1.78–2.07 (m, 5H), 1.70 (br d, 1H, J=13.1Hz); $^{13}$C NMR (50 MHz, CDCl$_3$) d 197.24, 173.04, 169.94, 152.91, 144.21, 131.21, 129.53, 118.43, 66.17, 52.04, 48.90, 48.90, 47.85, 37.90, 32.15, 26.22, 23.44, 21.12.

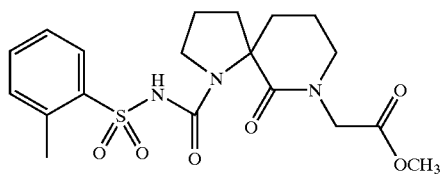

The same method as for the preparation of 15a was employed. Thus, acylation of crude spirocyclic methyl ester hydrochloride 10b (465 mg, 1.77 mmol) with isocyanate (295 mL; 1.95 mmol)) in CH$_2$Cl$_2$ (20 mL) afforded 24a as a white solid (405 mg, 54.0% over 4 steps) after flash chromatography (SiO$_2$; 1/9 MeOH/EtOAc, R$_f$ 0.20): mp 125–128° C. (softens at 78–110° C.); IR (CH$_2$Cl$_2$ cast) 3400 (br w), 3333 (br w), 2953 (w), 2877 (w), 1745 (m), 1684 (m), 1637 (br s) cm⁻¹; ¹H NMR (200 MHz, CDCl₃) d 8.05 (d, 1H, J=8.2 Hz, Ar—H), 7.04–7.48 (m, 3H, Ar—H), 4.15–4.40 (m, 1H), 3.40–3.79 (m, 4H), 3.63 (br s, 3H, OCH₃), 3.04–3.23 (m, 1H), 2.45–2.72 (m, 1H), 2.66 (s, 3H, CH₃), 2.10–2.32 (m, 1H), 1.55–2.10 (m, 6H); ¹³C NMR (50 MHz, CDCl₃) d 172.57 (br s), 170.00, 136.93, 132.74 (br s), 132.15, 129.80 (br s), 125.96, 66.46 (br s), 52.09 (br s), 49.05 (br s), 48.76 (br s), 48.42 (br s), 37.75 (br s), 31.66 (br s), 23.40 (br s), 20.92, 20.01.

Free acid at the C-Terminus i.e. Hydrolysis:

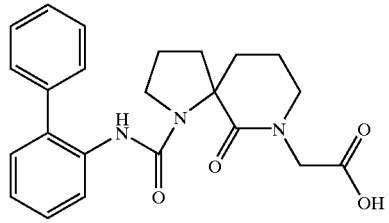

General Procedure Spirocyclic Urea Acid (16b). The same method as for the preparation of N-Cbz-spirocyclic acid 9 was employed. Thus, hydrolysis of methyl spirocyclic urea ester 16a (390 mg, 0.93 mmol) with 3M KOH (310 mL) in THF/H₂O (5/1 mL) afforded 16b (355 mg, 94%) as a white solid: mp 192–193° C.; IR (CDCl₃+CD₃OD cast) 3600–2500 (br w), 3429 (w), 3260 (w), 2950 (m), 2868 (w), 1732 (m), 1634 (s), 1611 (s) cm⁻¹; ¹H NMR (200 MHz, CDCl₃+CD₃OD) d 7.84 (br d, 1H, J=8.0 Hz, Ar—H), 7.18–7.42 (m, 5H, Ar—H), 7.02–7.20 (m, 2H, Ar—H), 6.95 (br dd, 1H, J=7.8, 7.2 Hz, Ar—H), 4.45 (d, 1H, J=17.6 Hz, 1×a-gly-CH₂), 3.52 (d, 1H, J=17.6 Hz, 1×a-gly-CH₂), 3.25–3.50 (m, 1H), 3.02–3.22 (m, 2H), 2.90–3.02 (m, 1H), 2.30–2.50 (m, 1H), 1.96–2.18 (m, 1H), 1.64–1.96 (m, 5H), 1.50–1.64 (br d, 1H, J=13.5Hz); ¹³C NMR (50 MHz, CDCl₃+CD₃OD) d 173.14, 170.75, 153.31, 138.19, 135.18, 132.10, 129.42, 128.89, 128.74, 127.87, 127.57, 123.00, 121.00, 65.74, 48.64, 48.49, 46.70, 37.19, 31.91, 23.06, 20.68.

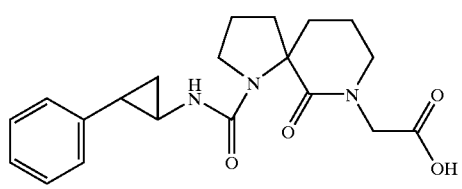

The same method as for the preparation of N-Cbz-spirocyclic acid 9 was employed. Thus, hydrolysis of methyl spirocyclic urea ester 17a (430 mg, 1.12 mmol) with 3M KOH (750 mL) in THF/H₂O/CH₃OH (5/1/1 mL) afforded 17b (384 mg, 92%) as a white solid: mp 108–111° C. (softens at 90° C.); IR (CDCl₃+CD₃OD cast) 3650–2200 (br w), 3316 (br m), 2923 (s), 2853 (m), 1728 (m), 1629 (br s) cm⁻¹.

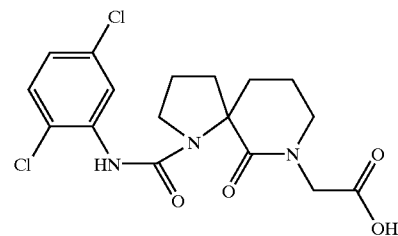

The same method as for the preparation of N-Cbz-spirocyclic acid 9 was employed. Thus, hydrolysis of methyl spirocyclic urea ester 18a (390 mg, 0.93 mmol) with 3M KOH (310 mL) in THF/H₂O (5/1 mL) afforded 18b (355 mg, 94%) as a white solid: mp 192–193° C.; IR (CDCl₃+CD₃OD cast) 3428 (w), 2949 (w), 2857 (w), 1742 (s), 1676 (m), 1644 (s) cm⁻¹; ¹H NMR (200 MHz, CDCl₃) d 8.32 (d, 1H, J=2.6 Hz, Ar—H), 7.19 (d, 1H, J=8.8 Hz, Ar—H), 6.89 (br s, 1H, NH), 6.86 (dd, 1H, J=8.8, 2.6 Hz, Ar—H), 4.69 (d, 1H, J=17.5 Hz, 1×a-gly-CH₂), 3.71 (s, 3H, OCH₃), 3.54–3.74 (m, 3H), 3.60 (d, 1H, J=17.5 Hz, 1×a-gly-CH₂), 3.21–3.33 (m, 1H), 2.72 (ddd, 1H, J=12.6, 12.2, 5.4 Hz), 2.21–2.44 (m, 1H), 1.82–2.23 (m, 5H), 1.74 (br d, 1H, J=12.8 Hz); ¹³C NMR (50 MHz, CDCl₃) d 172.72, 169.91, 152.25, 136.72, 133.41, 129.21, 122.64, 120.15, 119.77, 66.29, 52.00, 48.80, 48.80, 47.78, 38.16, 32.33, 23.46, 21.24.

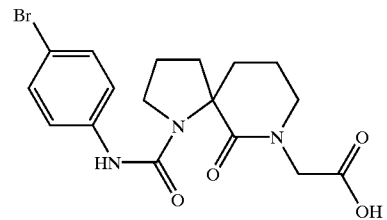

The same method as for the preparation of N-Cbz-spirocyclic acid 9 was employed. Thus, hydrolysis of methyl spirocyclic urea ester 19a (390 mg, 0.93 mmol) with 3M KOH (310 mL) in THF/H₂O (5/1 mL) afforded 19b (355 mg, 94%) as a white solid: mp 192–193° C.; IR (CDCl₃+CD₃OD cast) 3332 (br w), 2952 (w), 2869 (w), 1749 (m), 1638 (s), 1591 (m) cm⁻¹; ¹H NMR (200 MHz, CDCl₃) d 7.31 (d, 2H, J=9.6 Hz, Ar—H), 7.25 (d, 2H, J=9.6 Hz, Ar—H), 6.58 (br s, 1H, NH), 4.69 (br d, 1H, J=17.2 Hz, 1×a-gly-CH₂), 3.72 (s, 3H, OCH₃), 3.48–3.68 (m, 3H), 3.20–3.33 (m, 1H), 2.72 (br ddd, 1H, J=12.4, 12.2, 5.6 Hz), 2.14–2.37 (m, 1H), 1.80–2.12 (m, 5H), 1.73 (br d, 1H, J=13.0 Hz); ¹³C NMR (50 MHz, CDCl₃) d 173.11, 170.08, 153.27, 138.39, 131.62, 121.48, 115.13, 66.15, 52.07, 48.89, 48.89, 47.87, 38.16, 32.47, 23.52, 21.35.

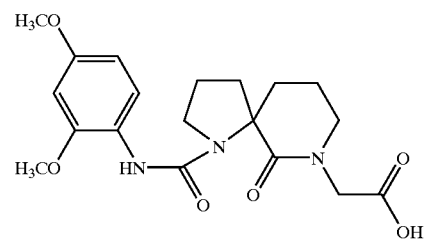

The same method as for the preparation of N-Cbz-spirocyclic acid 9 was employed. Thus, hydrolysis of methyl spirocyclic urea ester 20a (390 mg, 0.96 mmol) with 3M KOH (890 mL) in THF/H₂O/MeOH (5/1/1 mL) afforded 20b (quant.) as a white solid: mp 50–52° C.; IR (CDCl₃ cast) 3600–2400 (br w), 3436 (w), 2942 (m), 1732 (m), 1649 (br m), 1614 (m), 1527 (s) cm⁻¹; ¹H NMR (200 MHz, CDCl₃) d 10.09 (br s, 1H), 7.72 (br d, 1H, J=8.0 Hz, Ar—H), 6.67 (br s, 1H, NH), 6.35 (d, 1H, J=2.2 Hz, Ar—H), 6.32 (dd, 1H, J=8.0, 2.2 Hz, Ar—H), 4.32 (d, 1H, J=17.6 Hz, 1×a-gly-CH₂), 3.87 (d, 1H, J=17.6 Hz, 1×a-gly-CH₂), 3.72 (s, 3H, OCH₃), 3.66 (s, 3H, OCH₃), 3.38–3.70 (m, 3H), 3.04–3.18 (m, 1H), 2.28–2.52 (m, 1H), 2.12–2.28 (m, 1H), 1.60–2.12 (m, 6H); ¹³C NMR (50 MHz, CDCl₃) d 173.14, 170.20, 155.55, 153.62, 149.14, 121.18, 120.41, 103.66, 98.09, 65.82, 55.44, 55.18, 50.02, 48.84, 46.99, 36.87, 32.42, 23.35, 20.79.

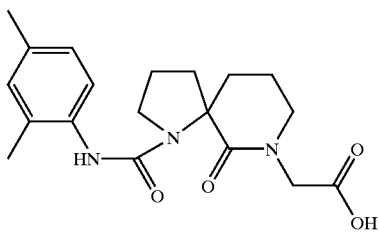

The same method as for the preparation of N-Cbz-spirocyclic acid 9 was employed. Thus, hydrolysis of methyl spirocyclic urea ester 21a (372 mg, 1.00 mmol) with 3M KOH (664 mL) in THF/H₂O/MeOH (5/2/1 mL) afforded 21b (348 mg, 97%) as a white solid: mp ° C.; IR (CDCl₃+CD₃OD cast) 3650–2500 (w), 2970 (m), 1738 (br s), 1638 (m) cm⁻¹; ¹H NMR (200 MHz, CDCl₃+CD₃OD) d 7.16 (br d, 1H, J=7.8 Hz, Ar—H), 6.83 (m, 2H, Ar—H), 4.28 (d, 1H, J=17.6 Hz, 1×a-gly-CH₂), 3.68 (d, 1H, J=17.4 Hz, 1×a-gly-CH₂), 3.31–3.57 (m, 3H), 3.04–3.19 (m, 1H), 2.37–2.55 (m, 1H), 2.15 (s, 3H, CH₃), 2.09 (s, 3H, CH₃), 1.61–2.32 (m, 7H); ¹³C NMR (50 MHz, CDCl₃) d 173.52, 170.82, 154.42, 134.27, 133.59 & 133.52, 131.39 & 131.24, 130.72, 126.66, 124.75 & 124.59, 65.91, 49.05, 48.69, 47.17, 37.33, 32.21, 23.34, 20.85, 20.39, 17.31.

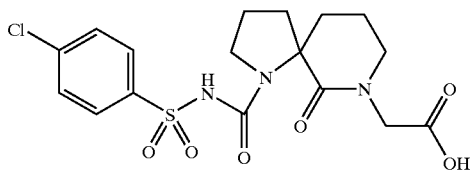

The same method as for the preparation of N-Cbz-spirocyclic acid 9 was employed. Thus, hydrolysis of methyl spirocyclic urea ester 22a (390 mg, 0.93 mmol) with 3M KOH (310 mL) in THF/H₂O (5/1 mL) afforded 22b (355 mg, 94%) as a white solid: mp 192–193° C.; IR (CDCl₃+CD₃OD cast) 3333 (br w), 2953 (w), 2877 (w), 1748 (m), 1670 (m), 1651 (s), 1635 (s) cm⁻¹; ¹H NMR (200 MHz, CDCl₃) d 7.78–8.03 (m, 2H, Ar—H), 7.28 & 7.36 (d, 2H, J=8.0 Hz, Ar—H), 3.95–4.28 (m, 1H), 3.66 (br s, 3H, OCH₃), 3.35–3.95 (m, 4H), 3.05–3.24 (m, 1H), 2.34–2.60 (m, 1H), 2.06–2.30 (m, 1H), 1.70–2.06 (m, 5H), 1.50–1.70 (m, 1H); ¹³C NMR (50 MHz, CDCl₃) d peaks were not resolved.

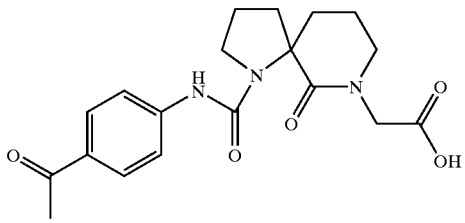

The same method as for the preparation of N-Cbz-spirocyclic acid 9 was employed. Thus, hydrolysis of methyl spirocyclic urea ester 23a (390 mg, 0.93 mmol) with 3M KOH (310 mL) in THF/H₂O (5/1 mL) afforded 23b (355 mg, 94%) as a white solid: mp 192–193° C.; IR (CDCl₃+CD₃OD cast) 3329 (br w), 2950 (w), 1748 (m), 1654 (br s), 1587 (m) cm⁻¹; ¹H NMR (200 MHz, CDCl₃) d 7.77 (d, 2H, J=8.8 Hz, Ar—H), 7.43 (d, 2H, J=8.8 Hz, Ar—H), 7.18 (br s, 1H, NH), 4.64 (d, 1H, J=17.5 Hz, 1×a-gly-CH₂), 3.68 (s, 3H, OCH₃), 3.48–3.72 (m, 4H), 3.17–3.31 (m, 1H), 2.70 (ddd, 1H, J=12.4, 12.4, 5.2 Hz), 2.47 (s, 3H, CH₃), 2.07–2.29 (m, 1H), 1.78–2.07 (m, 5H), 1.70 (br d, 1H, J=13.1Hz); ¹³C NMR (50 MHz, CDCl₃) d 197.24, 173.04, 169.94, 152.91, 144.21, 131.21, 129.53, 118.43, 66.17, 52.04, 48.90, 48.90, 47.85, 37.90, 32.15, 26.22, 23.44, 21.12.

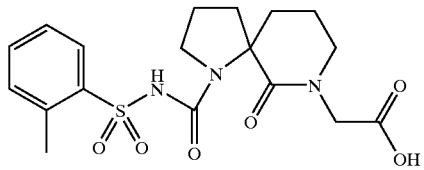

The same method as for the preparation of N-Cbz-spirocyclic acid 9 was employed. Thus, hydrolysis of methyl spirocyclic urea ester 24a (390 mg, 0.93 mmol) with 3M KOH (310 mL) in THF/H₂O (5/1 mL) afforded 24b (355 mg, 94%) as a white solid: mp 192–193° C.; IR (CDCl₃+CD₃OD cast) 3400 (br w), 3333 (br w), 2953 (w), 2877 (w), 1745 (m), 1684 (m), 1637 (br s) cm⁻¹; ¹H NMR (200 MHz, CDCl₃) d 8.05 (d, 1H, J=8.2 Hz, Ar—H), 7.04–7.48 (m, 3H, Ar—H), 4.15–4.40 (m, 1H), 3.40–3.79 (m, 4H), 3.63 (br s, 3H, OCH₃), 3.04–3.23 (m, 1H), 2.45–2.72 (m, 1H), 2.66 (s, 3H, CH₃), 2.10–2.32 (m, 1H), 1.55–2.10 (m, 6H); ¹³C NMR (50 MHz, CDCl₃) d 172.57 (br s), 170.00, 136.93, 132.74 (br s), 132.15, 129.80 (br s), 125.96, 66.46 (br s), 52.09 (br s), 49.05 (br s), 48.76 (br s), 48.42 (br s), 37.75 (br s), 31.66 (br s), 23.40 (br s), 20.92, 20.01.

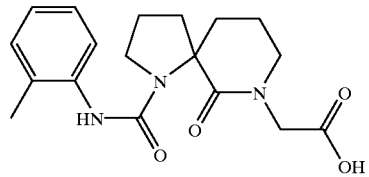

The same method as for the preparation of N-Cbz-spirocyclic acid 9 was employed. Thus, hydrolysis of methyl spirocyclic urea ester 15a (283 mg, 0.79 mmol) with 3M KOH (788 mL) in THF/H₂O/MeOH (5/1/1 mL) afforded 15b (quant.) as a white solid: mp 184–185° C.; IR (CDCl₃+CD₃OD) 3600–2400 (br m), 3299 (br m), 2950 (m), 2870 (m), 1729 (m), 1636 (s), 1608 (s) cm⁻¹; ¹H NMR (200 MHz, CDCl₃+CD₃OD) d 7.31 & 7.32 (br d, 1H, J=7.5 Hz, Ar—H), 6.95–7.06 (m, 2H, Ar—H), 6.88 & 6.89 (br dd, 1H, J=7.5, 7.2 Hz, Ar—H), 4.28 (d, 1H, J=17.4 Hz, 1xa-gly-CH$_2$), 3.66 (d, 1H, J=17.4 Hz, 1xa-gly-CH$_2$), 3.28–3.62 (m, 3H), 3.02–3.16 (m, 1H), 2.35–2.54 (m, 1H), 2.00–2.22 (m, 1H), 2.11 (s, 3H, CH$_3$), 1.58–2.00 (m, 6H); $^{13}$C NMR (50 MHz, CDCl$_3$+CD$_3$OD) d 173.36, 170.64, 154.08 & 154.04, 136.28 & 136.19, 130.95 & 130.77, 129.97, 126.01, 124.41, 124.28 & 124.11, 65.82, 48.95, 48.56, 47.10, 37.23, 32.03, 23.23, 21.73, 17.28.

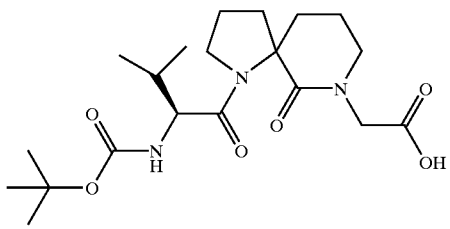

The same method as for the preparation of N-Cbz-spirocyclic acid 9 was employed. Thus, hydrolysis of methyl valine spirocyclic ester 14a (335 mg, 0.79 mmol) with 3M KOH (790 mL) in THF/H$_2$O/MeOH (5/1/1 mL) afforded 14b (quant.) as a white solid: mp 45–47° C.; IR (CDCl$_3$ cast) 3600–2300 (br w), 3312 (br w), 2968 (m), 1707 (s), 1636 (br s) cm$^1$; $^1$H NMR (200 MHz, CDCl$_3$) d 9.90 (br s, 1H), 5.10–5.70 (m, 1H), 3.40–4.38 (m, 6H), 2.78–3.24 (m, 1H), 1.44–2.49 (m, 9H), 1.32 (br s, 9H, C(CH$_3$)$_3$), 0.74–0.95 (m, 6H, (CH$_3$)$_2$); $^{13}$C NMR (50 MHz, CDCl$_3$) many peaks, contained peaks for rotomers of diastereomers.

Examples from the Libraries:

Bicyclic Spirolactam (720 compounds): The following is a table of MS (MH+) data for libraries containing the bicyclic spirolactam.

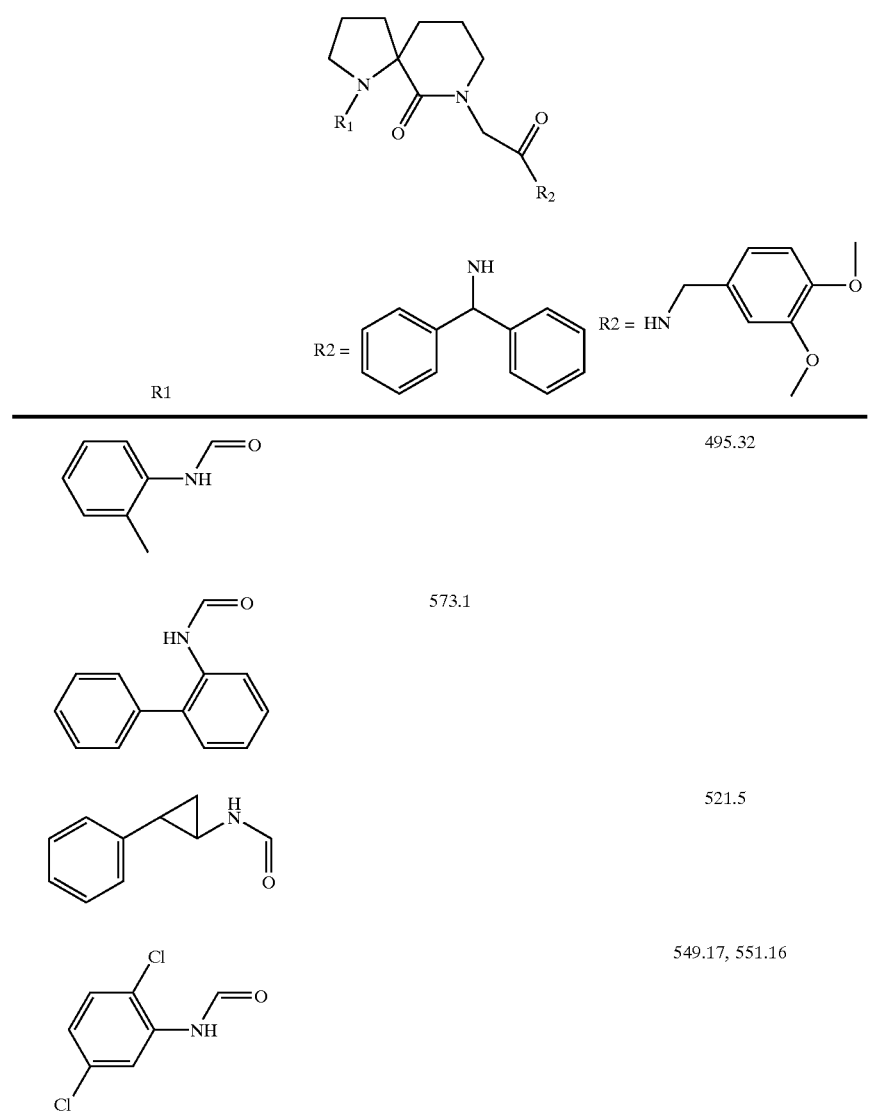

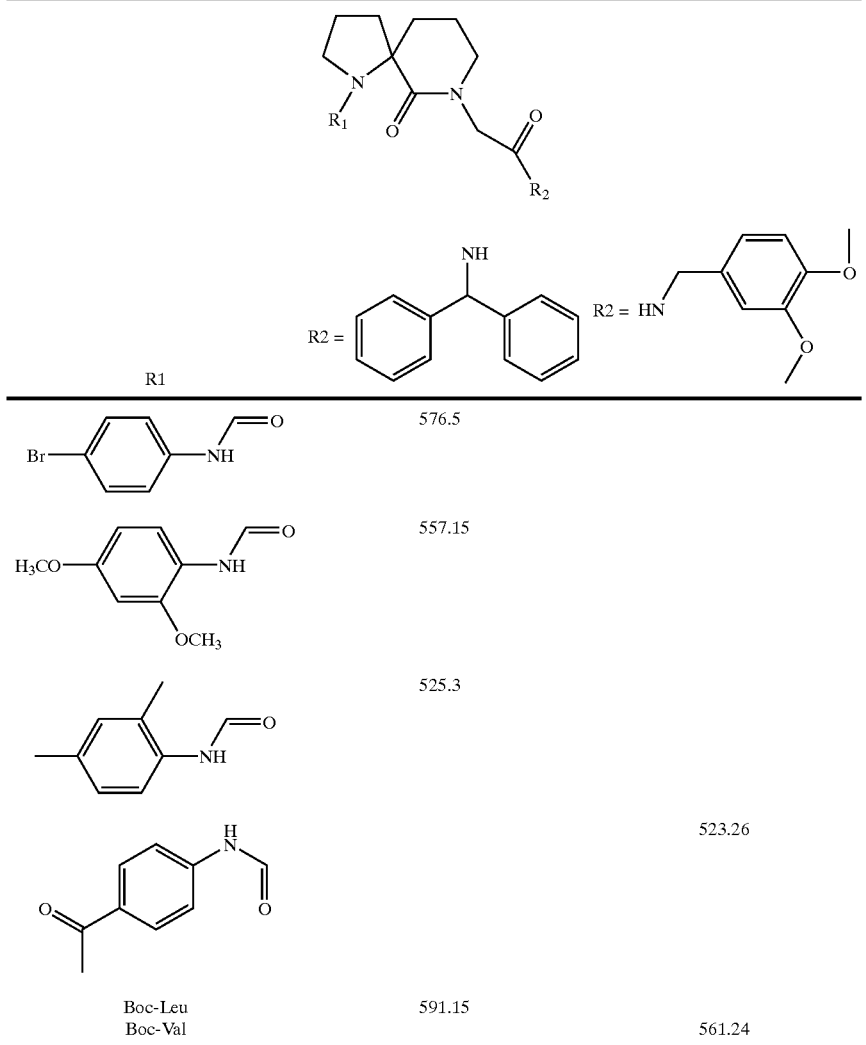

| R1 | | |
|---|---|---|
| 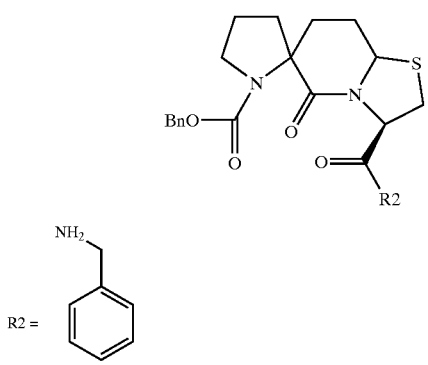 (Br-phenyl-NH-CHO) | 576.5 | |
| (H3CO-, OCH3 phenyl-NH-CHO) | 557.15 | |
| (dimethylphenyl-NH-CHO) | 525.3 | |
| (acetyl-phenyl-NH-CHO) | | 523.26 |
| Boc-Leu | 591.15 | |
| Boc-Val | | 561.24 |

Tricyclic Spirolactam (80 compounds): From TLC, each of the four diastereomers could be visualized. One MS example is included:

MH+=479.90

(structure with BnO-C(=O)-N-spirocycle-thiazolidine-C(=O)-R2)

R2 = benzylamine (NH2-CH2-phenyl)

EXAMPLE 3

Preparation of Methyl N-Cbz-Spirocyclic Ester (1)

a) (S)-N-Cbz-Proline tert-Butyl Ester

An ice-cooled (0° C.) stirred solution of (S)-proline tert-butyl ester (2) (24.5 g, 143 mmol) and anhydrous diisopropylethylamine (DIPEA) (32.4 mL, 186 mmol) in dry THF (400 mL) was treated with benzylchloroformate (24.6 mL, 172 mmol). After 5 min, the cooling bath and removed and the reaction mixture was stirred at room temperature for 6 h. The mixture was poured into ether (500 mL) and 1 N HCl (400 mL). The organic fraction was washed with $H_2O$ (200 mL) and brine (200 mL), and dried over $MgSO_4$. The solvent was removed in vacuo and the resultant oil (43.0 g; 99% was used without further purification. A portion (1 g) was purified by flash chromatography ($SiO_2$; 10% EtOAc in hexane, $R_f$ 0.25) yielding a clear colorless oil (990 mg): $^1H$ NMR (200 MHz, $CDCl_3$) δ 7.22–7.42 (m, 5H, Ar—$\underline{H}$), 5.02–5.22 (m, 2H, $OCH_2$), 4.18–4.20 (m, 1H, α-CH), 3.40–3.65 (m, 2H, δ-$CH_2$), 2.10–2.24 (m, 1H), 1.80–2.10 (m, 3H), 1.35 & 1.43 (s, 9H, $C(C\underline{H}_3)_3$).

b) N-Cbz-2-Allylproline tert-Butyl Ester (4)

To a cooled stirred solution (−78° C.) of protected proline 3 (2.0 g, 7.60 mmol) in THF (30 rnL) was added 2 M lithium diisopropyl amine (4.2 rnL, 8.40 mmol). After 30 min, allyl bromide (723 mL, 8.40 mmol) was added dropwise. The resultant mixture was warmed to −40° C. and stirred for 2 h. The mixture was partitioned between $CH_2Cl_2$ (200 mL) and $H_2O$ (200 mL). The organic fraction was dried over $MgSO_4$ and the solvent removed in vacuo. The residue was purified by flash chromatograghy ($SiO_2$; 50% EtOAc in hexane, R$f$ 0.60) to give 4 (1.44 g, 62.3%) as a clear oil: IR ($CH_2Cl_2$ cast) 3071 (w), 3032 (w), 2976 (m), 2932 (m), 1731 (s), 1702 (s) cm$^{-1}$; $^1$H NMR (200 MHz, CDCl$_3$) δ 7.20–7.42 (m, 5H, Ar—H), 5.58–5.82 (m, 1H, CH═CH$_2$), 4.93–5.22 (m, 4H, OCH$_2$ & CH═CH$_2$), 3.58–3.80 (m, 1H, 1×δ-CH$_2$), 3.34–3.50 (m, 1H, 1×δ-CH$_2$), 3.08 & 2.90 (ddt, 1H, J=14.2, 6.6, 1.2 Hz, 1×CH$_2$—CH═), 2.45–2.65 (m, 1H, 1×CH$_2$—CH═), 1.92–2.15 (m, 2H, β-CH$_2$), 1.70–1.92 (m, 2H, γ-CH$_2$), 1.33 & 1.39 (s, 9H, C(CH$_3$)$_3$); $^{13}$C NMR (50 MHz, CDCl$_3$) δ 173.04, 154.45 & 154.15, 137.10 & 136.26, 133.65 & 133.17, 128.29 & 128.28, 127.96 & 127.86, 127.71 & 127.66, 118.56, 80.96 & 80.82, 68.31 & 67.50, 66.94 & 66.30, 49.13 & 48.22, 38.98 & 37.86, 36.99 & 35.40, 27.60 & 27.56, 22.93 & 22.32.

c) N-Cbz-2-(Hydroxypropyl)proline tert-Butyl Ester (5)

To a cooled stirred solution (0° C.) of allylproline 4 (2.0 g, 5.90 mmol) in THF (30 mL) was added 1 M BH$_3$ THF (2.2 mL, 2.20 mmol). The reaction mixture was monitored for the disappearance of olefin by TLC (15/84 EtOAc/Hexane). After 30 min, an additional 1 mL of BH$_3$ THF was added and stirring was continued for 30 min. The reaction was quenched and oxidized by the careful dropwise addition of $H_2O$ (3.4 mL), 3 N KOH (3.6 mL), and 30% (aq) $H_2O_2$ (3.6 mL). After 45 min at 0° C., the mixture poured into EtOAc (300 mL) and $H_2O$ (150 mL). The aqueous fraction was extracted with EtOAc (2×100 mL). The combined organic fractions were dried (MgSO$_4$) and concentrated to yield a clear oil (1.92 g, 91.4%), which could be used without further purification. The alcohol could be purified by flash chromatography (SiO$_2$; 8/2 EtOAc/hexane, R$f$ 0.40) to yield 5 as a clear oil: IR ($CH_2Cl_2$ cast) 3448 (br m), 3032 (w), 2973 (m), 2875 (m), 1728 (s), 1700 (s) cm$^{-1}$; 1H NMR (200 MHz, CDCl$_3$) δ 7.20–7.36 (m, 5H, Ar—H), 5.16 & 5.19 (d, 1H, J=12.0 Hz, 1×C(O)OCH$_2$), 4.94 & 4.99 (d, 1H, J=12.0 Hz, 1×C(O)OCH$_2$), 3.38–3.78 (m, 2H, δ-CH$_2$), 3.47 & 3.59 (br t, 2H, J=7.0 Hz, CH$_2$OH), 2.59 (br s, 1H, OH), 1.65–2.38 (m, 6H), 1.20–1.64 (m, 2H), 1.31 & 1.34 (s, 9H, C(CH$_3$)$_3$); $^{13}$C NMR (50 MHz, CDCl$_3$) δ 173.52 & 173.43, 154.73 & 154.47, 136.94 & 136.23, 128.34, 128.11 & 127.95, 127.78 & 127.73, 81.00 & 80.90, 68.78 & 67.99, 66.99 & 66.46, 62.59 & 62.48, 49.22 & 48.34, 37.33 & 35.85, 30.78 & 29.83, 27.58, 26.86 & 26.75, 22.94 & 22.41.

d) N-Cbz-2-(Formylpropyl)proline tert-Butyl Ester (6)

Dry DMSO (9.90 mL, 139 mmol) was added dropwise over 5 min to a stirred cooled (−78° C.) solution of distilled oxalyl chloride (6.3 imL, 73.1 mmol) in $CH_2Cl_2$ (150 mL). After 20 min, a solution of the alcohol 5 (26.6 g, 73.1 mmol) in $CH_2Cl_2$ (50 mL) was added over 3 h. The resultant slurry was stirred for 30 min at −78° C. and then dry diisopropylethylamine (32.0 mL, 183 mmol) was injected dropwise over 3 h. Stirring was continued at −78° C. for 30 min, the cold bath removed, and after a further 30 min, $H_2O$ (100 mL) was added. The mixture was stirred for a further 10 min and the aqueous layer was extracted with $CH_2Cl_2$ (2×400 mL). The combined organic layers were washed with 10% v/v aqueous HCl (2×100 mL), saturated aqueous NaHCO$_3$ (2×100 mL), and brine (1×100 mL), dried over MgSO$_4$, and evaporated in vacuo. The residue (26.0 g, 98.5%) could be used without further purification or purified (1 g) by flash chromatograghy (SiO$_2$; 2/8 EtOAc/hexane, R$_f$ 0.32) to give 6 (880 mg, 88%) as a clear oil: IR ($CH_2Cl_2$ cast) 3032 (w), 2975 (m), 2880 (m), 1719 (s), 1698 (s) cm$^{-1}$; $^1$H NMR (200 MHz, CDCl$_3$) δ 9.52 & 9.61 (t, 1H, J=2.0 Hz, CHO), 7.18–7.36 (m, 5H, Ar—H, 5.12 & 5.18 (d, 1H, J=10.0 Hz, 1×OCH$_2$), 4.93 & 4.99 (d, 1H, J=11.5 Hz, 1×OCH$_2$:), 3.51–3.78 (m, 1H, 1×δ-CH$_2$), 3.32–3.48 (rn, 1H, 1×δ-CH$_2$), 2.32–2.64 (m, 2H), 1.70–2.32 (m, 6H), 1.30 & 1.32 (s, 9H, C(CH$_3$)$_3$); $^{13}$C NMR (50 MHz, CDCl$_3$) δ 202.05 & 201.20, 172.61 & 172.46, 154.47 & 154.44, 136.90 & 136.89, 128.27 & 128.21, 128.08 & 127.93, 127.69 & 127.60, 81.16 & 80.99, 68.11 & 67.38, 66.96 & 66.41, 49.00 & 48.08, 39.02 & 38.63, 37.14 & 35.96, 27.42, 27.02 & 26.75, 22.82 & 22.15.

e) N-Cbz-2-(3'-[N-(O-methyl)glycyl]propyl)proline tert-Butyl Ester (7)

To a stirred solution of glycine methyl ester hydrochloride (1.25 g, 9.94 mmol) in anhydrous MeOH (17 mL) was added dropwise dry diisopropylethylamine (3.3 mL, 18.9 mmol) followed by a solution of aldehyde 6 (3.42 g, 9.46 mmol) in dry MeOH (10 mL). MgSO$_4$ (500 mg) was added to the stirring solution after 30 min and 5 h. The resultant slurry was cooled to −4° C. and NaBH$_4$ (573 mg, 15.1 mmol) was added portionwise. The reaction was quenched after 10 min with sat. NaHCO$_3$ (10 mL) and $H_2O$ (50 mL). The aqueous fraction was extracted with EtOAc (3×200 mL). The combined organic fractions were dried (MgSO$_4$) and concentrated to yield a clear oil (4.2 g), which was purified by flash chromatography (SiO$_2$; 40×205 mm, 100% EtOAc, R$f$ 0.20) to yield dialkylated material (1.6 g, 39%) and desired amine 7 (2.42, 59%) as viscous oils: Data for desired product: IR ($CH_2Cl_2$ cast) 3335 (br w), 2973 (m), 2877 (w), 1731 (s), 1701 (s) cm$^{-1}$; $^1$H NMR (200 MHz, CDCl$_3$) δ 7.21–7.39 (m, 5H, Ar—H), 5.14 & 5.20 (d, 1H, J=12.0 Hz, 1×OCH$_2$), 4.94 & 5.01 (d, 1H, J=12.0 Hz, 1×OCH$_2$), 3.57–3.79 (m, 1H, 1×δ-CH$_2$), 3.69 (s, 3H, OCH$_3$), 3.39–3.52 (m, 1H, 1×δ-CH$_2$), 3.33 (d, 2H, J=12.2 Hz), 2.58 (t, 1H, J=7.0 Hz), 2.12–2.52 (m, 2H), 1.90–2.12 (m, 2H), 1.63–1.90 (m, 3H), 1.31 & 1.34 (s, 9H, (CH$_3$)$_3$), 1.25–1.57 (m, 2H)); $^{13}$NMR (50 MHz, CDCl$_3$ δ 173.51 & 173.42, 172.90 & 172.87, 154.65 & 154.33, 137.13 & 136.41, 128.39, 128.17 & 127.96, 127.83, 80.96 & 80.82, 68.78 & 68.03, 66.94 & 66.42, 51.65, 50.72 & 50.63, 49.68 & 49.51, 49.30 & 48.39, 37.45 & 35.90, 32.17 & 31.21, 27.68, 24.41 & 24.16, 23.11 & 22.50.

f) N-Cbz-2-(3'-[N-(O-methyl)glycyl]propyl)proline Hydrochloride (8)

To a stirred solution of tert-butyl ester 7 (2.81 g, 6.48 mmol) in $CH_2Cl_2$ (30 mL) was added trifluoroacetic acid (30 mL). The solvent was removed after 5 h. THF (30 mL) was added and removed in vacuo. An additional 30 mL of THF and 1 N HCl (6.5 mL) were added and removed in vacuo. The resultant residue was used without further purification: $^1$H NMR (200 MHz, CDCl$_3$) 0 7.98 (br s, 1H, OH), 7.18–7.38 (m, SH, Ar—H), 5.02–5.21 (m, 2H, OCH$_2$), 3.42–3.97 (m, 4H), 3.78 (s, 3H, OCH$_3$), 3.00–3.20 (m, 2H), 1.68–2.42 (m, 8H).

g) Methyl N-Cbz-spirocyclic Ester (1)

Method A) To a cooled solution 0° C. of crude amino acid hydrochloride 8 (3.51 g, 8.45 mmol) and DIPEA (1.6 mL, 8.45 rnmol) in $CH_2Cl_2$ (400 mL) was added 2-chloro-1-methyl pyridinium iodide (2.45 g, 9.31 mmol) portionwise, followed by DIPEA (3.55 mL, 21.1 mmol). The reaction mixture was allowed to warm to room temperature. After 2 h, the solvent was removed in vacuo and the residue was purified by flash chromatography (SiO$_2$; 40/60 $CH_2Cl_2$/EtOAc, R$f$ 0.40) to yield a clear oil (2.42 g, 79.4% over 2 steps): IR ($CH_2Cl_2$ cast) 3484 (br m), 3032 (w), 2951 (m), 2873 (m), 1748 (s), 1694 (s), 1647 (s) cm$^{-1}$; $^1$H NMR (200 MHz, CDCl$_3$) δ 7.22–7.40 (m, 5H, Ar—H), 5.02 & 5.09 & 5.14 (d, 2H, J=12.4Hz, OCH$_2$), 4.29 & 4.65 (d, 1H, J=17.2 Hz, 1×α-gly-CH$_2$), 3.71 & 3.66 (s, 3H, OCH$_3$), 3.61 & 3.25 (d, 1H, J=17.2 Hz, 1×α-gly-CH$_2$), 3.50–3.65 & 3.20–3.25 & 2.95–3.04 (m, 4H), 2.52–2.65 & 2.21–2.40 (m, 2H), 1.66–2.08 (m, 6H); $^{13}$C NMR (50 MHz, CDCl$_3$) δ 172.86, 169.85 & 169.56, 154.25, 136.82 & 136.58, 128.55 & 128.39, 128.39 & 128.08, 127.78 & 127, 64, 67.11 & 66.52, 65.65 & 65.12, 51.98 & 51.92, 48.86 & 48.70, 48.70 & 48.57, 48.29 & 48.10, 39.36 & 38.34, 33.04 & 32.01, 23.18 & 22.59, 21.06.

Method B) To a cooled solution 0° C. of crude amino acid hydrochloride 8 (7.8 g, 18.9 mmol) and N-methylmorpholine (4.4 mL, 39.6 mmol) in CH$_2$Cl$_2$ (800 mL) was added EDCI (4.0 g, 20.9 mmol) portionwise. The reaction mixture was allowed to warm to room temperature. After 24 h, the solvent volume was reduced to 500 mL. The solution was washed with 1 N HCl (100 mL), H$_2$O (100 mL), dried (MgSO$_4$) and concentrated to yield a viscous oil (5.48 g, 88.4% over 2 steps) with identical spectral data to that isolated from procedure A, and the material could be used without further purification.

EXAMPLE 4

Preparation of N-Cbz-Spirocyclic Acid (9)

A solution of methyl N-Cbz-spirocyclic ester 1 (1.43 g, 3.97 mmol) in distilled THF (20 mL) and H$_2$O (5 mL) was treated with aqueous 3M KOH (2.03 mL), and the mixture was stirred for 4 h at RT. The resultant clear solution was acidified with 1 N HCl to pH 5 and extracted with EtOAc (3×200 mL). The organic fractions were combined, dried (MgSO$_4$), and concentrated to a tacky solid (1.30 g, 94.0%), which was used without further purification (as a mixture of diastereomers): $^1$H NMR (200 MHz, CDCl$_3$) δ 7.23–7.38 (m, 5H, Ar—H), 6.39 (br s, 1H, OH), 5.10 & 5.14 (d, 1H, J=12.4 Hz, 1×OCH$_2$), 4.97 & 5.04 (d, 1H, J=12.4 Hz, 1×OCH$_2$), 4.00–4.42 (m, 2H, α-gly-CH$_2$), 3.50–3.68 & 3.20–3.38 & 2.95–3.10 (m, 4H), 2.18–2.55 (m, 2H), 1.70–2.10 (m, 6H); $^{13}$C NMR (50 MHz, CDCl$_3$) δ 173.95 & 173.31, 171.66 & 170.88, 154.89 & 154.18, 136.44, 128.83 & 128.55, 128.55 & 128.34, 128.10 & 127.93, 67.44 & 6.726, 65.86 & 65.24, 50.33, 49.33 & 49.04, 48.63 & 48.04, 39.37 & 37.66, 33.17 & 32.20, 23.35 & 22.68, 21.02 & 20.89.

EXAMPLE 5

Preparation of Methyl Spirocyclic Ester (10)

The N-Cbz-spirocyclic ester 1 (989 mg, 2.74 mmol) was hydrogenolyzed in MeOH (20 mL) in the presence of Pearlman's catalyst (20% Pd(OH)$_2$/C) under an atmosphere of H$_2$. The catalyst was then removed by filtration through Celite and the solvent evaporated to give an oil (610 mg, 98%), which was used without further purification: $^1$H NMR (200 MHz, CDCl$_3$) δ 4.14 & 4.25 (d, 2H, J=17.2 Hz, 1×α-gly-CH$_2$), 3.83 & 3.95 (d, 2H, J=17.2 Hz, 1×α-gly-CH$_2$), 3.72 (s, 3H, OCH$_3$), 3.05–3.80 (m, 3H), 2.85–3.05 (m, 1H), 2.00–2.26 (m, 1H), 1.65–2.00 (m, 7H); $^{13}$C NMR (50 MHz, CDCl$_3$) δ 175.21, 169.53, 65.24, 52.16, 49.33, 49.11, 47.43, 38.10, 34.31, 26.20, 20.18.

EXAMPLE 6

General Procedure for Preparation of Library Using N-hydroxysuccinimide a) To a cooled solution 0° C. of crude spirocyclic acid (1.18 g, 3.42 mmol) and N-hydroxysuccinimide (590 mg, 5.13 mmol) in THF (40 mL) was added EDCI (983 mg, 5.13 mmol), then a catalytic amount of DMAP (10 mg). The reaction mixture was allowed to warm to room temperature. After 48 h, the reaction mixture was poured into EtOAc (250 mL) and washed with H$_2$O (50 mL), brine (50 mL), dried over MgSO$_4$, and evaporated in vacuo. The residue (1.50 g, 99%) was used without further purification.

b) Library synthesis. An aliquot (300 μL) of a 75 mM stock solution (24 mL) of the activated N-hydroxysuccinimide ester in 1,2-dichloroethane was added to each of 80 wells in a 96-well microtiter plate containing one equivalent of an amine in 0.5 M pyridine solution. The plate was shaken on a bench-top shaker until all the reactions were completed as determined by TLC. Each well was washed with an equal volume of H$_2$O. The remaining organic solutions were concentrated yielding the desired compounds. Data for 11: $^1$H NMR (200 MHz, CDCl$_3$) δ 8.05 (m, 1H), 7.14–7.36 (m, 10H, Ar—H), 5.09 (d, 1H, J=16.8 Hz, 1×α-gly-CH$_2$), 4.81 (d, 1H, J=13.0 Hz, 1×OCH$_2$), 4.58 (d, 1H, J=13.0 Hz, 1×OCH$_2$), 4.52 (dd, 1H, J=15.0, 6.2 Hz, 1×NCH$_2$), 4.37 (dd, 1H, J=15.0, 4.8 Hz, 1×NCH$_2$), 3.50–3.66 (m, 3H), 3.29 (d, 1H, J=16.8 Hz, 1×α-gly-CH$_2$), 3.15–3.26 (m, 1H), 2.22–2.38 (m, 2H), 1.70–2.10 (m, 6H).

EXAMPLE 7

General Procedure for Preparation of Methyl Spirocyclic Urea Ester (12)

To a solution of crude spirocyclic methyl ester hydrochloride 10b (400 mg, 1.52 mmol) and DIPEA (398 μL, 2.28 mmol) in CH$_2$Cl$_2$ (15 mL) was added 2-methylphenylisocyanate (208 μL, 1.67 mmol). The reaction mixture was stirred at RT for 3 d. The solvent volume was removed in vacuo, and the residue was purified by flash chromatography (SiO$_2$; 100% EtOAc, Rf 0.35) to yield a white solid (298 mg, 54.6% over 4 steps): mp 169–171° C.; IR (CH$_2$Cl$_2$ cast) 3318 (br w), 2950 (w), 2868 (w), 1748 (m), 1638 (s) cm$^{-1}$; $^1$H NMR (200 MHz, CDCl$_3$) δ 7.60 (br d, 1H, J=7.8 Hz, Ar—H), 7.02–7.16 (m, 2H, Ar—H), 6.91 (br dd, 1H, J=7.8, 7.2 Hz, Ar—H), 6.14 (br s, 1H, NH), 4.69 & 4.70 (d, 1H, J=17.2 Hz, 1×αgly-CH$_2$), 3.64 & 3.66 (s, 3H, OCH$_3$), 3.42–3.64 (m, 3H), 3.41 & 3.61 (d, 1H, J=17.2 Hz, 1×α-gly-CH$_2$), 3.12–3.26 (m, 1H), 2.60–2.78 (m, 1H), 2.14–2.36 (m, 1H), 2.17 & 2.18 (s, 3H, CH$_3$), 1.77–2.14 (m, 5H), 1.62–1.77 (br d, 1H, J=12.8 Hz); $^{13}$C NMR (50 MHz, CDCl$_3$) δ 172.99, 169.96, 153.65, 136.90, 130.04, 128.83, 126.38, 123.65, 122.89, 65.94, 51.77, 48.66, 48.60, 47.63, 37.99, 32.58, 23.41, 21.24, 17.57.

EXAMPLE 8

General Procedure for Preparation of Methyl Spirocyclic Dipeptide Ester (13)

To a cooled solution 0° C. of crude spirocyclic methyl ester 10a (91.1 mg, 403 μmol), N-Boc-Leu-OH H$_2$O (201 mg, 806 μmol), and HOBt (82 mg, 605 μmol) in DMF (4 mL) was added NMM (66 μL, 605 , umol), then EDCI (116 mg, 605 μmol). The reaction mixture was allowed to warm to room temperature. After 24 h, the solvent volume was removed in vacuo, and the residue was purified by flash chromatography (SiO$_2$; 100% EtOAc, Rf 0.30) to yield a white solid (124 mg, 69.8%): IR (MeOH cast) 3338 (br w), 2958 (m), 2870 (w), 1752 (m), 1708 (s), 1641 (s) cm$^{-1}$; $^1$H NMR (200 MHz, CDCl$_3$) δ 4.90–5.60 (m, 1H), 4.10–4.59 (m, 1H), 3.41 & 3.45 (s, 3H, OCH$_3$), 3.01–3.80 (m, 6H), 1.20–2.20 (m, 8H), 1.19 (br s, 9H, C(CH$_3$)$_3$), 0.60–1.01 (m, 9H); $^{13}$C NMR (50 MHz, CDCl$_3$) many peaks, contained peaks for rotomers of diastereomers.

EXAMPLE 9

General Procedure for Preparation of Library Using Isobutyl Chloroformate a) To a cooled solution –23° C. of crude spirocyclic acid (800 mg, 2.31 mmol) and NMM (403 μL, 2.31 mmol) in CHCl$_3$ (15 mL) was added isobutylchloroformate (300 μL, 2.31 mmol). After 1 h, the reaction mixture was washed quickly with ice-cold H$_2$O (20 mL), dried over MgSO$_4$, filtered to a final volume of 24 mL, and stored at –23° C. This material was used directly without isolation.

b) Library .synthesis. An aliquot (300 μL) of a 96 mM cooled (–23° C.) mixed anhydride stock solution (24 mL) was added to each of 80 wells in a 96-well microtiter plate containing one equivalent of an amine in 0.5 M pyridine solution. The plate was shaken on a bench-top shaker for 1 h. The organic solutions were concentrated yielding the desired compounds.

EXAMPLE 10

Synthesis of Tricyclic Lactams

Compounds of Formula Ia in which X=S and p is 1 can also be prepared by use of cysteine (either D or L form) in a modification of the general technique described in Example 1. Thus, for example, as depicted in Scheme 3, compound 6 of Scheme 1 can be condensed with a carboxy-protected cysteine derivative (such as the methyl ester) to form a thiazolidine (compound 29), which can then be cyclized to yield a compound of Formula Ia, in which X is S and p=1 (e.g., compound 30).

Scheme 3

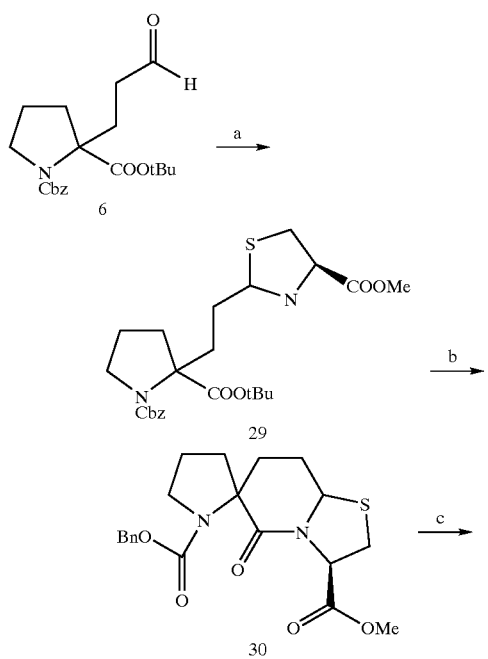

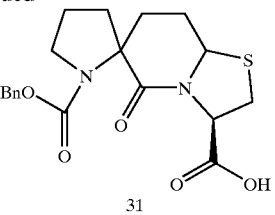

Reagents: (a) L-Cysteine-OMe, NaOH (94%) (b) (i) TFA/CH$_2$Cl$_2$ (ii) 2-chloro-N-methyl pyridinium iodide, diisopropylethylamine (98% for two steps) (c) KOH (aq).

Preparation of Tricyclic Spirolactam 30 a) Methyl 2-[2'-[N-Cbz-2"-tert-butoxycarbonyl)-pyrrolidinyl]ethyl]thiazolidine-4-carboxylate (29)

To an ice-cooled (0° C.) stirred solution of (S)-cysteine methyl ester hydrochloride (1.63 g, 9.52 mmol) in H$_2$O (20 mL) was added 1 M NaOH (aq) (9.53 mL), followed by a solution of aldehyde 6 (3.44 g, 9.52 mmol) in EtOH (60 mL). The reaction mixture was stirred at room temperature overnight. The mixture was poured into H$_2$O and extracted with EtOAc (2×200 mL). The combined organic fractions were washed with brine (100 mL), dried over MgSO$_4$, and filtered. The solvent was removed in vacuo and the resultant tar was purified by flash chromatography (SiO$_2$; 40% EtOAc in hexane, R$_f$0.25 yielding a clear colorless tar (4.30 g, 94%): The $^1$H NMR (200 MHz, CDCl$_3$) of the product was highly complex, apparently as a result of formation of a mixture of 4 diastereomers. This material was used without further separation in the next step.

b) Tricyclic Spirolactam 30 i) To a stirred solution of tert-butyl ester 29 (prepared in step a) above) 3.68 g, 7.69 mmol) in CH$_2$Cl$_2$ 930 mL) was added trifluoroacetic acid (30 mL). The solvent was removed after 5 h. THF (30 mL) was added and removed in vacuo. An additional 30 mL of THF and 1 N HCl (7.7 mL) were added and removed in vacuo. The resultant residue was used without further purification.

ii) To an ice-cooled (0° C.) stirred solution of amino acid (7.69 mmol) in CH$_2$Cl$_2$ (400 mL) from previous step was added diisopropyl ethyl amine (DIPEA) (1.34 mL; 7.69 mmol), followed by 2-chloro-N-methyl pyridinium iodide (2.23 g, 8.46 mmol). An additional amount of DIPEA (3.36 mL; 19.2 mmol) was added. The reaction mixture was removed from the cold bath and stirred at room temperature for 2 h. The solvent was removed in vacuo and the resultant tar was purified by flash chromatography (SiO$_2$; 40% EtOAc in hexane, R$^f$0.25) yielding a clear colorless tar (3.03 g, 98% for two steps): $^1$H NMR (200 MHz, CDCl$_3$) was complex, apparently a mixture of 4 diastereomers was present. MS cal'd 404.48, expt 405.2.

EXAMPLE 11

Synthesis of a Spirolactam Peptidomimetic

A peptidomimetic of the invention, having the structure Ac-Pro-Arg-Pro-Leu-spirolactam-Ala-Pro-Gly-OH was synthesized as follows:

H$_2$N-Ala-Pro-Gly-OtBu was prepared according to conventional peptide chemistry techniques and commercially available protected peptides. The partially-protected N-terminal peptide Ac-Pro-Arg(Pbf)-Pro-Leu-OH was obtained from Macromolecular Resources (Boulder, Colo.) (Pbf=protecting group: pentamethyldihydrobenzofuran-5-sulfonyl). Spirocyclic lactam 9 or 31 (see Examples 4 and 10) having a free "C-terminal" carboxyl group, was converted to the N-hydroxysuccinimide ester under standard conditions, and then coupled with H$_2$N-Ala-Pro-Gly-OtBu under standard EDCI coupling conditions (EDCI, HOBt, NMM) in 70% yield. The "N-terminal" amine was deprotected by hydrogenolysis (H$_2$, Pd/C) in 95% yield, and the "N-terminal" peptide Ac-Pro-Arg(Pbf)-Pro-Leu-OH was coupled under EDCI coupling conditions (46% yield). At this stage, the diastereomers at the spirolactam moiety could be resolved by chromatography (e.g., preparative thin-layer chromatography). Finally, the protecting groups of the Arg residue and the C-terminal carboxy group were removed by treatment with trifluoroacetic acid in dichloromethane (98% yield) to provide the desired spirolactam-containing compound.

Alternatively, Boc-Spiro-OMe, e.g. compounds 1 or 30, were treated with TFA in methylene chloride followed by treatment with Boc-Leu-OH, under standard EDCI coupling conditions (EDCI, HOBt, NMM) to afford Boc-L-Spiro-OMe in 45–89% yields. Treatment of Boc-L-Spiro-OMe with TFA in methylene chloride followed by treatment with Ac-PR(Pbf)P-OH under standard EDCI coupling conditions afforded Ac-P-R(PBf)-P-L-Spiro-OMe. Subsequent treatment with LiOH/THF/MeOH, followed by H$_2$N-APG-OtBu under standard EDCI coupling conditions and treatment with TFA in methylene chloride to afford Ac-P-R-P-L-Spiro-A-P-G-OH compounds:

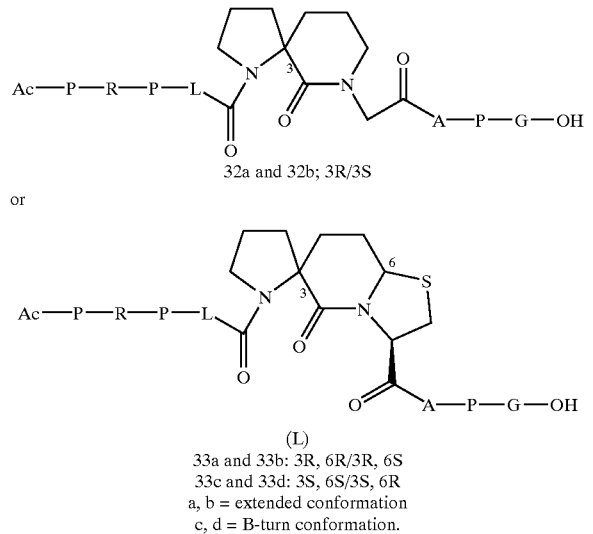

32a and 32b; 3R/3S or (L)
33a and 33b: 3R, 6R/3R, 6S
33c and 33d: 3S, 6S/3S, 6R
a, b = extended conformation
c, d = B-turn conformation.

EXAMPLE 12

Screening Assays

Compounds of the invention were tested for ability to bind to SH3 domains as follows. Under standard binding assay conditions, the control nonamers Ac-PRPLPVAPG-OH (SEQ ID NO:3) and Ac-APALPPKPP-OH (SEQ ID NO:4) (Ac=acetyl, —OH denotes the "C-terminus"), which correspond to the proline-rich—and C-terminal regions of p85, respectively, can be compared against two peptides with identical terminal amino acid sequences, in which the Pp portion of the consensus sequence has been replaced with a spirolactam moiety of the invention (viz., Ac-PRPL-spirolactam-APG-OH and Ac-APAL-spirolactam-KPP-OH, respectively). For example, test compounds can include a spirolactam in which (referring to Formula I) R$_1$ is the tetrapeptide residue Ac-PRPL (SEQ ID NO:1) or Ac-APAL (SEQ ID NO:2), R$_3$ and R$_4$ are both H, m and n are both 1, R$_2$ is —C(R$_{2a}$)(R$_{2b}$)C(O)R$_5$, R$_{2a}$ and R$_{2b}$ are both H, and R$_5$ is a tripeptide residue, e.g., APG-OH or KPP-OH. The IC$_{50}$ of the spirolactam analogs of the invention for an SH3 domain of interest are measured, and the measured values are compared to the values for the control ligands.

The assay is performed by measuring the binding of a GST-lyn (residues 1–131) fusion protein immobilized on a plate, with a biotinylated peptide whose sequence is derived from the N-terminal proline-rich SH3 binding domain of p85 (amino acid residues 83–98 which correspond to the regulatory subunit of PI3-kinase) in the presence of test compounds. The results are then compared with the appropriate controls (no compound; with or without any solvent used to dissolve the compound, e.g., DMF DMSO; control to exclude irrelevant peptide binding, etc.) to assess the specific binding to the SH3 domain of the lyn fusion protein. It will be appreciated that other fusion proteins incorporating p85 peptides (e.g., lacZ-p85) may be used in the assay.

In an exemplary procedure, ninety-six well polystyrene plates are coated overnight with 100 µl GST-lyn-SH3 fusion protein (10 µg/ml) and subsequently washed three times with 400 µl phosphate-buffered saline (PBS). Wells are blocked with 300 µl 5% BSA for two hours at room temperature and washed three times with 400 µl PBS. 100 µl of approximately 100 µM of each of the test compounds is added to the separate wells (yielding a final concentration of about 50 µM compound) and incubated for 15 minutes at room temperature, followed by the addition of 100 µl of 1 µg/ml biotinylated p85 proline-rich peptide. The plate is then incubated for a further two hours at room temperature, followed by another washing step as before. 100 µl of streptavidin-alkaline phosphatase (Jackson Immuno Research Labs, West Grove, Pa.) is then added, incubated for one hour at 4° C. and washed as before. 200 µl para-nitrophenyl phosphate (Sigma Co., St. Louis, Mo.) is then added and the optical density of the plate wells read at 405 nm after a standard interval of between 30 minutes and two hours.

Using this assay, specific binding of the p85 peptide to the SH3 domain can be measured, and any specific effects of compounds on this binding can be demonstrated.

The ability of spirolactams to bind to SH3 domains was assessed by measuring their ability to inhibit the binding of cononical proline-rich peptide to purified Lyn SH3 domain. This inhibition was measured by surface plasmon resonance.

Lyn SH3-GST fusion proteins were generated as previously described (Pleiman, et al., *Mol & Cellular Biol.* 13(9):5877 (1993)), purified from bacterial lysates by glutathione affinity chromatography and eluted by competition. Aggregates were removed by size exclusion chromatography on Sephadex 75 (Pharmacia Biotech, Uppsala, Sweden).

Surface plasmon resonance measurements were performed on a BIAcore 2000 biosensor (BIAcore AB, Uppsala, Sweden). A synthetic canonical proline-rich peptide derived from phosphatidylinositol 3 kinase p85 (Pleiman, et al., (1994) *Science* 263:1609 (1994)); GGGK-PRPPRPLPVAPGSS (SEQ ID NO:5) was immobilized on a prepared streptavidin coated sensor chip (Sensor Chip SA, BIAcore AB) via an N-terminal biotin moiety at a density of 0.05 pmol/mm$^2$. All experiments were conducted at 25° C. in the running buffer HBS (0.01 M HEPES, pH 7.4, 0.15 M NaCl, 3.4 mM EDTA, 0.005% surfactant P20). Monomeric Lyn SH3-GST fusion protein (1 µM) was injected over the peptide surface at a rate of 30 µl/min. for 4.5 minutes. Dissociation was monitored during subsequent washing of the chip with running buffer for an additional 5.0 minutes. Regeneration of the peptide surface was accomplished with a 10 second pulse of 5 mM NaOH.

To test their activity, 0.01–100 µM spirolactam or non-biotinylated canonical peptide was incubated with the fusion protein prior to injection. Data were recorded in real-time as sensorgrams and analyzed subsequently using BIA evaluation 2.0 software (BIAcore AB).

TABLE 4

Relative binding affinity to SH3 domain

| Peptides | Percent Binding | Peptides | Percent Binding |
|---|---|---|---|
| Ac-GGGKPRPPRPLPVAP-GSS-OH | 81 | 33a/b[b] (3S, 6S or 6R) | 85 |
| Ac-PRPLPVAPG-OH | nd | 33c/d[b] (3R, 6S or 6R) | 57 |
| 32a/b[a] (3S or 3R) | 58 | 33c/d[b] (3R, 6S or 6R) | 58 |

TABLE 4-continued

Relative binding affinity to SH3 domain

| Peptides | Percent Binding | Peptides | Percent Binding |
|---|---|---|---|
| 32a/b[a] (3S or 3R) | 61 | | |
| 33a/b[b] (3S, 6S or 6R) | 83 | | |

[a]Mass spectral data for 8a/b: cal'd 943, found MH$^+$ 944;
[b]Mass spectral data for 9a-d: cal'd 987, found MH$^+$ 988;
nd = not determined.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

The contents of all publications cited herein are hereby incorporated by reference.

Other embodiments are within the following claims.

What is claimed is:

1. A compound represented by the formula:

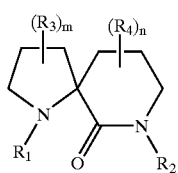

in which

R$_1$ is alkyl, aryl, alkylcarbonyl, arylcarbonyl, aminocarbonyl, N-substituted carbonylamino, alkoxycarbonyl, aryloxycarbonyl, alkylsulforyl, arylsulfonyl, amino acyl; N-substituted aminoacyl, or a peptide group;

R$_2$ is alkyl, aryl, or —C(R$_{2a}$)(R$_{2b}$)C(O)R$_5$;

R$_{2a}$ and R$_{2b}$ are each independently alkyl, aryl; or a side-chain moiety of a naturally occurring amino acid other than glycine, or R$_{2a}$ and R$_{2b}$, taken together with the carbon atom to which they are attached, form a 3 to 8 membered carbocyclic or heterocyclic ring; wherein the spirocyclic carbon atom is of the R configuration;

R$_3$ and R$_4$ are each, independently for each occurrence, hydrogen, halogen, alkyl, amino, hydroxy, alkoxy, cyano, or trifluoromethyl;

R$_5$ is hydroxy, alkyl, aryl, amino, alkoxy, aryloxy, —SH, alkylthio, peptide or arylthio; m and n are each independently 1 or 2; or a salt thereof.

2. The compound of claim 1, in which R$_1$ is a tetrapeptide.

3. The compound of claim 2, in which the tetrapeptide is Ac-Pro-Arg-Pro-Leu (SEQ ID NO: 1) or Ac-Ala-Pro-Ala-Leu (SEQ ID NO:2).

4. The compound of claim 1, in which R$_1$ is an amino acyl residue selected from the group consisting of Boc-Leu and Boc-Val.

5. The compound of claim 1, in which R$_1$ is an aminocarboxy moiety represented by the formula —C(O)NHR$_7$, in which R$_7$ is an aryl moiety or a bulky alkyl group.

6. The compound of claim 1, in which R$_2$ is a moiety represented by the formula —C(R$_{2a}$)(R$_{2b}$)C(O)R$_5$.

7. The compound of claim 6, in which R$_{2b}$ or R$_{2a}$ is a side-chain moiety of a naturally occurring amino acid other than glycine.

8. The compound of claim 6, in which R$_5$ is a tripeptide moiety selected from the group consisting of Lys-Pro-Pro-OH and Ala-Pro-Gly-OH.

9. The compound of claim 1, in which R$_3$ is hydroxy.

10. A composition comprising a compound of claim 1, or a pharmaceutically acceptable salt thereof, in a pharmaceutically acceptable vehicle.

11. A library of compounds represented by the formula (Formula 1):

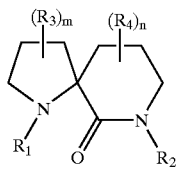

in which
- $R_1$ is alkyl, aryl, alkylcarbonyl, arylcarbonyl, aminocarbonyl, N-substituted carbonylamino, alkoxycarbonyl, aryloxycarbonyl, alkylsulfonyl, arylsulfonyl, amino acyl, N-substituted aminoacyl, or a peptide group;
- $R_2$ is alkyl, aryl, or —$C(R_{2a})(R_{2b})C(O)R_5$;
- $R_{2a}$ and $R_{2b}$ are each independently alkyl, aryl or a side-chain moiety of a naturally occurring amino acid other than glycine; or
- $R_{2a}$ and $R_{2b}$, taken together with the carbon atom to which they are attached, form a 3 to 8 membered carbocyclic or heterocyclic ring; wherein the spirocyclic carbon atom is of the R configuration;
- $R_3$ and $R_4$ are each, independently for each occurrence, hydrogen, halogen, alkyl, amino, hydroxy, alkoxy, cyano, or trifluoromethyl;
- $R_5$ is hydroxy, alkyl, aryl, amino, alkoxy, aryloxy, —SH, alkylthio, peptide or arylthio;
- m and n are each independently 1 or 2, or a salt thereof.

12. A method for inhibiting the binding of an SH3 binding signal transduction protein with an SH3 domain-containing protein comprising contacting the SH3 domain-containing protein with a compound represented by the formula (Formula I):

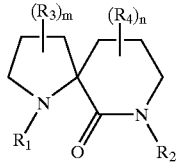

in which
- $R_1$ is alkyl, aryl, alkylcarbonyl, arylcarbonyl, aminocarbonyl, N-substituted carbonylamino, alkoxycarbonyl, aryloxycarbonyl, alkylsulfonyl, arylsulfonyl, amino acyl, N-substituted aminoacyl, or a peptide group;
- $R_2$ is alkyl, aryl, or —$C(R_{2a})(R_{2b})C(O)R_5$;
- $R_{2a}$ and $R_{2b}$ are each independently hydrogen, alkyl, aryl or a side-chain moiety of a naturally occurring amino acid other than glycine, or $R_{2a}$ and $R_{2b}$, taken together with the carbon atom to which they are attached, form a 3 to 8 membered carbocyclic or heterocyclic ring; wherein the spirocyclic carbon atom is of the R configuration;
- $R_3$ and $R_4$ are each, independently for each occurrence, hydrogen, halogen, alkyl, amino, hydroxy, alkoxy, cyano, or trifluoromethyl;
- $R_5$ is hydroxy, alkyl, aryl, amino, alkoxy, aryloxy, —SH, alkylthio, peptide or arylthio;
- m and n are each independently 1 or 2; or a salt thereof,
such that the compound binds to the SH3 domain-containing protein.

13. The method of claim 12, in which the SH3 domain is an SH3 domain of Lyn, wherein Lyn is an Src-related kinase.

14. The method of claim 12, in which $R_1$ is a tetrapeptide.

15. The method of claim 14, in which the tetrapeptide is Ac-Pro-Arg-Pro-Leu (SEQ ID NO:1) or Ac-Ala-Pro-Ala-Leu (SEQ ID NO:2).

16. The method of claim 12, in which $R_1$ is an amino acyl residue selected from the group consisting of Boc-Leu and Boc-Val.

17. The method of claim 12, in which $R_1$ is an aminocarboxy moiety represented by the formula —$C(O)NHR_7$, in which $R_7$ is an aryl moiety or a bulky alkyl group.

18. The method of claim 12, in which $R_2$ is a moiety represented by the formula —$C(R_{2a})(R_{2b})C(O)R_5$.

19. The method of claim 18, in which $R_{2b}$ is hydrogen and $R_{2a}$ is a side-chain moiety of a naturally occurring amino acid.

20. The method of claim 18, in which $R_5$ is a tripeptide moiety selected from the group consisting of Lys-Pro-Pro-OH and Ala-Pro-Gly-OH.

21. A method for inhibiting growth of a cell, the method comprising contacting the cell with an effective amount of a compound of claim 1 for a time and under conditions effective for the compound to bind to an SH3 domain-containing protein within the cell such that growth of the cell is inhibited.

22. The method of claim 12, wherein the SH3 domain-containing protein is a naturally occurring ligand to the SH3 binding signal transduction protein.

23. The method of claim 12, wherein the SH3-containing protein is present in a cancer cell.

24. The method of claim 12, wherein the SH3-containing protein is present in a fungal cell.

* * * * *

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: SH3 test peptide
<220> FEATURE:
<221> NAME/KEY: MISC_FEATURE
<222> LOCATION: (1)..(4)
<223> OTHER INFORMATION: Synthetic Peptide

<400> SEQUENCE: 1

Pro Arg Pro Leu
1

<210> SEQ ID NO 2
<211> LENGTH: 4
<212> TYPE: PRT
<213> ORGANISM: Artificial Sequence
<220> FEATURE:
<223> OTHER INFORMATION: SH3 test peptide
<220> FEATURE:
<221> NAME/KEY: MISC_FEATURE
<222> LOCATION: (1)..(4)
<223> OTHER INFORMATION: Synthetic Peptide

<400> SEQUENCE: 2

Ala Pro Ala Leu
1

<210> SEQ ID NO 3
<211> LENGTH: 9
<212> TYPE: PRT
<213> ORGANISM: Artificial Sequence
<220> FEATURE:
<223> OTHER INFORMATION: SH3 test peptide
<220> FEATURE:
<221> NAME/KEY: MISC_FEATURE
<222> LOCATION: (1)..(9)
```

```
<223> OTHER INFORMATION: Synthetic Peptide

<400> SEQUENCE: 3

Pro Arg Pro Leu Pro Val Ala Pro Gly
1               5

<210> SEQ ID NO 4
<211> LENGTH: 9
<212> TYPE: PRT
<213> ORGANISM: Artificial Sequence
<220> FEATURE:
<223> OTHER INFORMATION: SH3 test peptide
<220> FEATURE:
<221> NAME/KEY: MISC_FEATURE
<222> LOCATION: (1)..(9)
<223> OTHER INFORMATION: Synthetic Peptide

<400> SEQUENCE: 4

Ala Pro Ala Leu Pro Pro Lys Pro Pro
1               5

<210> SEQ ID NO 5
<211> LENGTH: 18
<212> TYPE: PRT
<213> ORGANISM: Artificial Sequence
<220> FEATURE:
<223> OTHER INFORMATION: SH3 test peptide
<220> FEATURE:
<221> NAME/KEY: MISC_FEATURE
<222> LOCATION: (1)..(18)
<223> OTHER INFORMATION: Synthetic Peptide

<400> SEQUENCE: 5

Gly Gly Gly Lys Pro Arg Pro Pro Arg Pro Leu Pro Val Ala Pro Gly
1               5                   10                  15

Ser Ser
```